United States Patent
McFadden et al.

(10) Patent No.: US 12,257,278 B2
(45) Date of Patent: Mar. 25, 2025

(54) METHODS OF TREATING CANCER WITH TNF EXPRESSING MYXOMA VIRUS

(71) Applicant: ARIZONA BOARD OF REGENTS ON BEHALF OF ARIZONA STATE UNIVERSITY, Scottsdale, AZ (US)

(72) Inventors: Douglas Grant McFadden, Tempe, AZ (US); John Christie, Portage, MI (US); Joseph Blattman, Scottsdale, AZ (US); Mohammed Masmudur Rahman, Chandler, AZ (US); Nancy Yaneth Villa, Scottsdale, AZ (US)

(73) Assignee: Arizona Board of Regents on behalf of Arizona State University, Scottsdale, AZ (US)

( * ) Notice: Subject to any disclaimer, the term of this patent is extended or adjusted under 35 U.S.C. 154(b) by 1023 days.

(21) Appl. No.: 17/259,849

(22) PCT Filed: Jul. 12, 2019

(86) PCT No.: PCT/US2019/041700
§ 371 (c)(1),
(2) Date: Jan. 12, 2021

(87) PCT Pub. No.: WO2020/014670
PCT Pub. Date: Jan. 16, 2020

(65) Prior Publication Data
US 2021/0268050 A1 Sep. 2, 2021

Related U.S. Application Data

(60) Provisional application No. 62/697,581, filed on Jul. 13, 2018.

(51) Int. Cl.
| | |
|---|---|
| A61K 35/768 | (2015.01) |
| A61K 35/14 | (2015.01) |
| A61K 35/28 | (2015.01) |
| A61K 45/06 | (2006.01) |
| A61P 35/00 | (2006.01) |
| C07K 14/525 | (2006.01) |

(52) U.S. Cl.
CPC ............ *A61K 35/768* (2013.01); *A61K 35/14* (2013.01); *A61K 35/28* (2013.01); *A61K 45/06* (2013.01); *A61P 35/00* (2018.01); *C07K 14/525* (2013.01)

(58) Field of Classification Search
CPC ............ A01K 2207/12; A61K 35/768; A61K 38/191; A61K 35/76; A61K 35/28; A61K 35/14; A61K 35/15; A61P 35/00; C07K 14/525; C12N 15/86; C12N 2710/24045; C12Q 1/70
See application file for complete search history.

(56) References Cited

U.S. PATENT DOCUMENTS

| | | | |
|---|---|---|---|
| 11,117,934 B2 * | 9/2021 | McFadden | ............ C07K 14/525 |
| 2013/0209406 A1 | 8/2013 | Tenoever | |
| 2014/0328804 A1 | 11/2014 | Mcfadden et al. | |
| 2018/0303886 A1 | 10/2018 | Hwang et al. | |
| 2019/0160115 A1 | 5/2019 | Falb et al. | |
| 2021/0061864 A1 | 3/2021 | McFadden et al. | |

FOREIGN PATENT DOCUMENTS

| | | |
|---|---|---|
| CN | 104039333 | 9/2014 |
| EP | 0972840 B1 | 5/2004 |
| WO | WO-2007143545 A2 | 12/2007 |
| WO | WO-2015078856 A1 | 6/2015 |
| WO | 2018049248 A1 | 3/2018 |
| WO | WO-2020014670 A1 | 1/2020 |
| WO | WO-2020037206 A1 | 2/2020 |
| WO | WO-2020051248 A1 | 3/2020 |
| WO | WO-2020198690 A1 | 10/2020 |
| WO | WO-2021046048 A1 | 3/2021 |
| WO | WO-2021046125 A1 | 3/2021 |

OTHER PUBLICATIONS

Balkwill. Tumour necrosis factor and cancer. Nat Rev Cancer 9(5):361-371 (2009).
Barrett et al. M135R is a Novel Cell Surface Virulence Factor of Myxoma Virus. Journal of Virology 81(1):106-114 (2007).
Bartee et al., Selective purging of human multiple myeloma cells from autologous stem cell transplant grafts using oncolytic myxoma virus. Biol Blood Marrow Transplant 18(10):1540-1551 (2012).
Bartee et al. The addition of tumor necrosis factor plus beta interferon induces a novel synergistic antiviral state against poxviruses in primary human fibroblasts. Journal of virology 83:498-511 (2009).
Burton et al. Targeting TNF-alpha for cancer therapy. J Biol 8:85 (2009).
Cameron et al., The complete DNA sequence of myxoma virus. Virology 264(2):298-318 (1999).
Chan et al., Oncolytic Myxoma Virus: The path to clinic. Vaccine 31(39):4252-4258 (2013).
Chan et al., Oncolytic Poxviruses. Annu Rev Virol 1(1):119-141 (2014).
Choi et al., Strengthening of antitumor immune memory and prevention of thymic atrophy mediated by adenovirus expressing IL-12 and GM-CSF. Gene Ther 19(7):711-723 (2012).
Coley. The treatment of malignant tumors by repeated inoculations of erysipelas: with a report of ten original cases. Am. J. Med. Sci. 105:487-511 (1893).

(Continued)

*Primary Examiner* — Bao Q Li
(74) *Attorney, Agent, or Firm* — Riverside Law LLP

(57) ABSTRACT

Disclosed herein, in certain embodiments, is a method of inhibiting or treating a cancer with use of a TNF expressing myxoma virus. Also disclosed herein are methods of inhibiting or treating a cancer with use of a mononuclear peripheral blood cells and/or a bone marrow cells treated with a TNF-expressing myxoma virus. Some aspects relate to engineered myxoma virus and pharmaceutical compositions for use with one or more of the methods described herein.

15 Claims, 16 Drawing Sheets

Specification includes a Sequence Listing.

(56) References Cited

OTHER PUBLICATIONS

Collin et al., The poxviral scrapin MV-LAP requires a myxoma viral infection context to efficiently downregulate MHC-I molecules. Virology 343(2):171-178 (2005).
Colombo et al.: Interleukin-12 in anti-tumor immunity and immunotherapy. Cytokine Growth Factor Rev. 13(2):155-168 (2002).
Del Vecchio et al., Interleukin-12: biological properties and clinical application. Clin Cancer Res 13(16):4677-4685 (2007).
GenBank Accession No. AF170726.2 (2019).
GenBank Accession No. EU552530 (2019).
GenBank Accession No. EU552531 (2019).
Guerin et al., Myxoma Virus Leukemia-Associated Protein is Responsible for Major Histocompatibility Complex Class I and Fas-CD95 Down-Regulation and Defines Scrapins, a New Group of Surface Cellular Receptor Abductor Proteins. J Virol 76(6):2912-2923 (2002).
Harrington et al., Optimizing Oncolytic Virotherapy in Cancer Treatment. Nat. Reviews Drug Discovery 19:689-706 (2019).
Hess et al., Antitumor efficacy of a human interleukin-12 expression plasmid demonstrated in a human peripheral blood leukocyte/human lung tumor xenograft SCID mouse model. Cancer Gene Ther 8(5):371-377 (2001).
Kashii et al., Constitutive expression and role of the TNF family ligands in apoptotic killing of tumor cells by human NK cells. J Immunol 163(10):5358-5366 (1999).
Kelly et al. History of oncolytic viruses: genesis to genetic engineering. Molecular Therapy 15:651-659 (2007).
Kim et al., Myxoma virus targets primary human leukemic stem and progenitor cells while sparing normal hematopoietic stem and progenitor cells. Leukemia 23(12):2313-2317 (2009).
Laverty et al., TGF-beta3 and cancer: a review. Cytokine Growth Factor Rev 20(4):305-317 (2009).
Lichty et al. Going viral with cancer immunotherapy. Nature Reviews Cancer 14:559-567 (2014).
Liu et al., The immunoregulatory properties of oncolytic myxoma virus and their implications in therapeutics. Microbes Infect 12(14-15):1144-1152 (2010).
Mansouri et al., The PHD/LAP-Domain Protein M153R of Myxomavirus is a Ubiquitin Ligase That Induces the Rapid Internalization and Lysosomal Destruction of CD4. J Virol 77(2):1427-1440 (2003).
Moriwaki et al., Differential roles of RIPK1 and RIPK3 in TNF-induced necroptosis and chemotherapeutic agent-induced cell death. Cell Death Dis 6(2):e1636 (2015).
Mossman et al. Myxoma virus M-T7, a secreted homolog of the interferon-gamma receptor, is a critical virulence factor for the development of myxomatosis in European rabbits. Virology 215:17-30 (1996).
Nayerossadat et al. Viral and nonviral delivery systems for gene delivery. Adv Biomed Res 1:27 (2012).
Neill et al., Decorin as a multivalent therapeutic agent against cancer. Adv Drug Deliv Rev 97:174-185 (2016).
Ogbomo et al., Myxoma Virus Infection Promotes NK Lysis of Malignant Gliomas In Vitro and In Vivo. PLoS One 8(6): e66825 (2013).
PCT/US2019/041700 International Search Report and Written Opinion dated Nov. 12, 2019.
PCT/US2020/049061 International Search Report and Written Opinion dated Dec. 7, 2020.
PCT/US2020/055083 International Search Report and Written Opinion dated Jan. 26, 2021.
Prevost-Blondel et al., Crucial Role of TNF-α in CD8 T Cell-Mediated Elimination of 3LL-A9 Lewis Lung Carcinoma Cells In Vivo. J Immunol 164(7): 3645-3651 (2000).
Rahman et al., Methods for Identifying Virus-Derived Serpins: Methods and Protocols. Methods in molecular biology 1826:73-86 (2018).
Russell et al. Oncolytic virotherapy. Nature Biotechn 30:658-670 (2012).
Stanford et al., Myxoma virus and oncolytic virotherapy: a new biologic weapon in the war against cancer. Expert Opin Biol Ther 7(9):1415-1425 (2007).
Stanford et al., Myxoma Virus Expressing Human Interleukin-12 Does Not Induce Myxomatosis in European Rabbits. Journal of Virology 81(22):12704-12708 (2007).
Sypula et al., Myxoma virus tropism in human tumor cells. Gene therapy & molecular biology 8:103-114 (2004).
U.S. Appl. No. 17/010,711 Non-Final Office Action dated Dec. 24, 2020.
Villa et al., Myxoma virus suppresses proliferation of activated T lymphocytes yet permits oncolytic virus transfer to cancer cells. Blood 125(24):3778-3788 (2015).
Wang et al., Infection of human cancer cells with myxoma virus requires Akt activation via interaction with a viral ankyrin-repeat host range factor. PNAS 103 (12): 4640-4645 (2006).
Wang et al. RIG-I Mediates the Co-Induction of Tumor Necrosis Factor and Type I Interferon Elicited by Myxoma Virus in Primary Human Macrophages. PLoS Pathog 4(7):e1000099 (2008).
Xu et al., The systemic delivery of an oncolytic adenovirus expressing decorin inhibits bone metastasis in a mouse model of human prostate cancer. Gene Ther 22(3):247-256 (2015).
Yao et al., Decorin-mediated inhibition of the migration of U87MG glioma cells involves activation of autophagy and suppression of TGF-β signaling. FEBS Open Bio 6(7):707-719 (2016).
Yu et al. Targeting Transmembrane TNF-α Suppresses Breast Cancer Growth. Cancer Res 73(13):4061-4075 (2013).
Zhang et al., Optimizing DC vaccination by combination with oncolytic adenovirus coexpressing IL-12 and GM-CSF. Mol Ther 19(8):1558-1568 (2011).
EP Application No. 19834625.6 Supplementary Partial European Search Report dated Mar. 15, 2022.
Sedger et al.: Poxvirus tumor necrosis factor receptor (TNFR)-like T2 proteins contain a conserved preligand assembly domain that inhibits cellular TNFR1-induced cell death. J Virol. 80(18):9300-9309 doi:10.1128/JVI.02449-05 (2006).
English translation of Chinese Office Action issued in App. No. CN201980059900, dated May 27, 2024, 7 pages.
Lilly et al., Ex vivo oncolytic virotherapy with myxoma virus arms multiple allogeneic bone marrow transplant leukocytes to enhance graft versus tumor. Molecular Therapy Oncolytics 4:31-40 (2016). URL: https://doi.org/10.1016/j.omto.2016.12.002.
Liu J, Wennier S, McFadden G. The immunoregulatory properties of oncolytic myxoma virus and their implications in therapeutics. Microbes Infect. Dec. 2010;12(14-15):1144-52. doi: 10.1016/j.micinf.2010.08.012. Epub Sep. 9, 2010. PMID: 20832500; PMCID: PMC2998584.
Office Action issued in App. No. IL280060, dated Jun. 25, 2024, 4 pages.
Spiesschaert B, McFadden G, Hermans K, Nauwynck H, Van de Walle GR. The current status and future directions of myxoma virus, a master in immune evasion. Vet Res. Jun. 9, 2011;42(1):76. doi: 10.1186/1297-9716-42-76. PMID: 21658227; PMCID: PMC3131250.

\* cited by examiner

Genetic map of Human TNF M135KO myxoma virus: vMyx-M135KO-hTNF

S E/L promoter | hTNF | S E/L promoter | eGFP | M136

M134 vMyx-Lau (WT) → vMyx-M135KO-hTNF

FIG. 2A vMyx-SODKO-hTNF-PBMC
DOSE RESPONSE

- - - - 1X10^6 PMBCsvMyx-SODKO-hTNF (1)
―――― 2X10^6 PMBCsvMyx-SODKO-hTNF (2)
―――― 4X10^6 PMBCsvMyx-SODKO-hTNF (3)
- - - - Control animals

FIG. 6

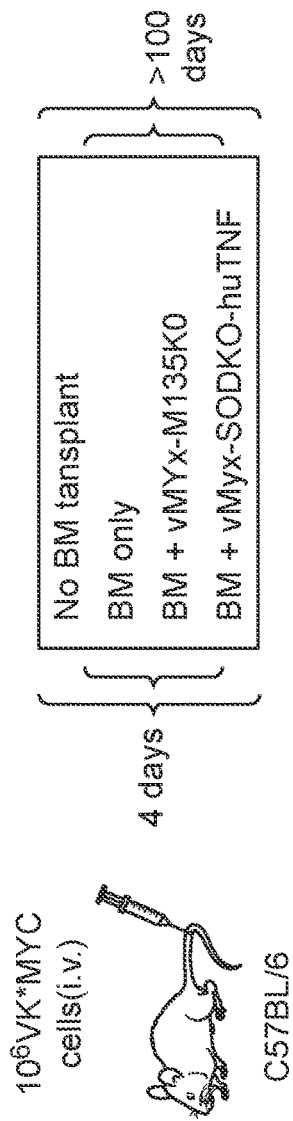
FIG. 13A
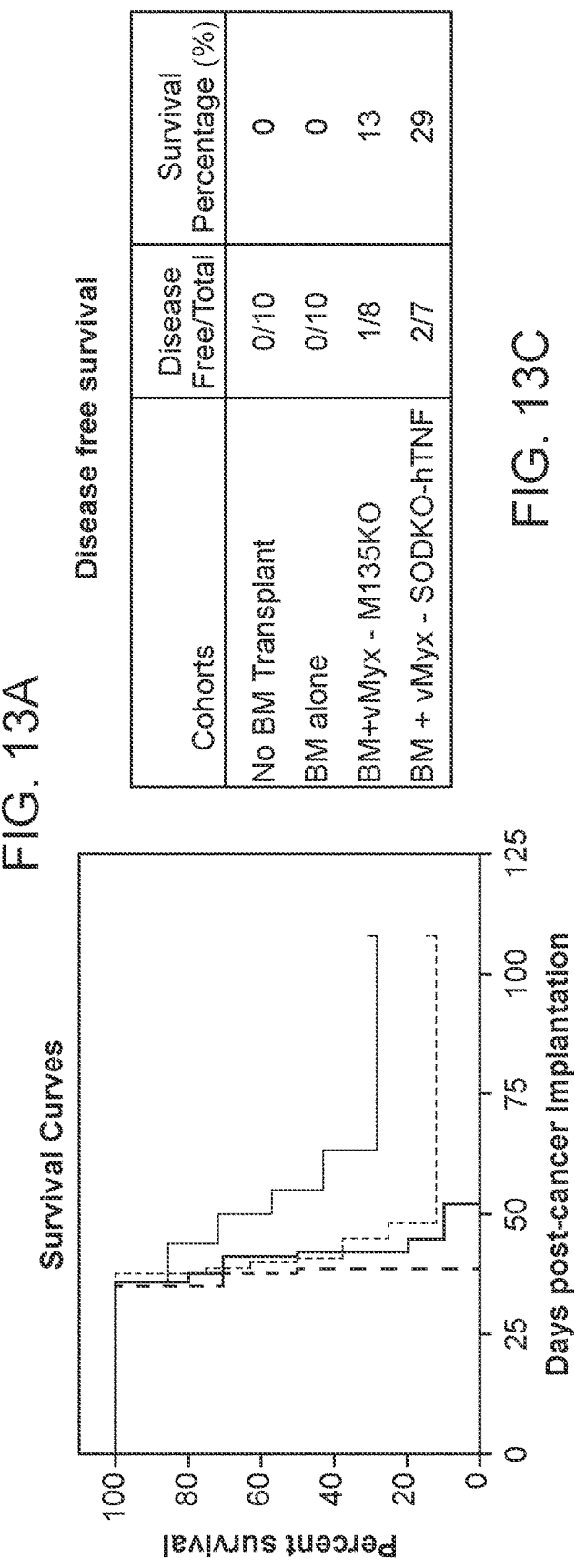
FIG. 13C
FIG. 13B

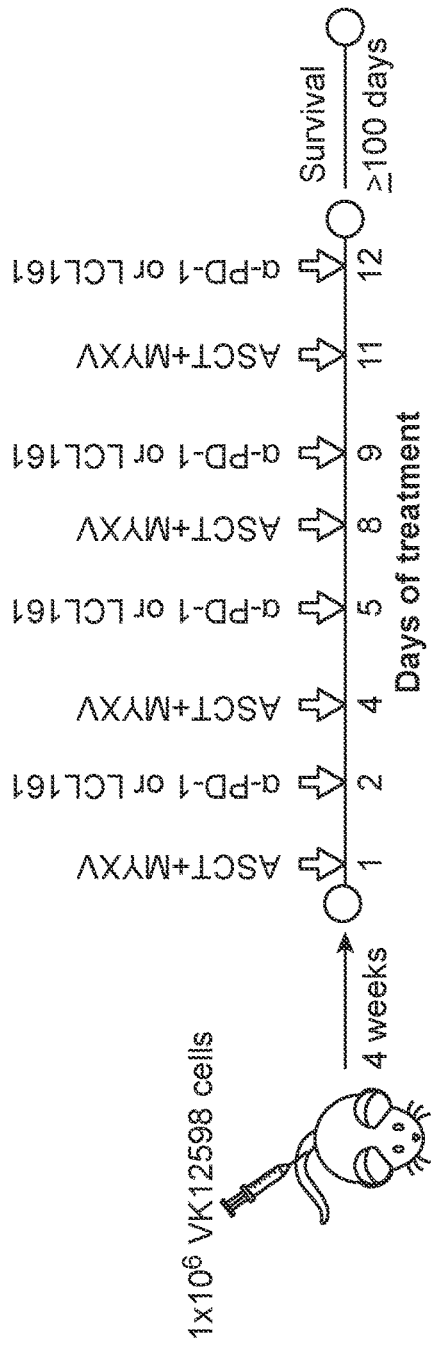
FIG. 14A
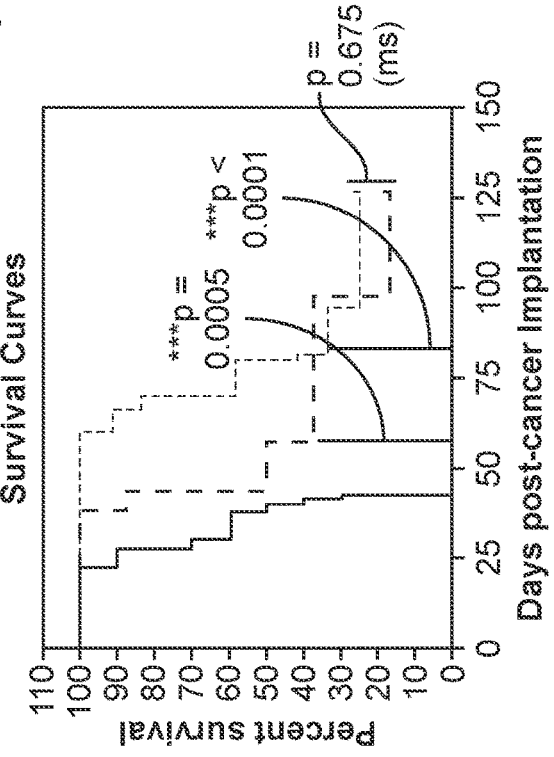
FIG. 14B
| Cohorts | Disease Free/Total | Survival Percentage (%) |
|---|---|---|
| No BM Transplant | 0/10 | 0 |
| BM + MYXV + α-PD-1 | 2/8 | 25 |
| BM + MYXV + LCL161 | 2/12 | 17 |
FIG. 14C

METHODS OF TREATING CANCER WITH TNF EXPRESSING MYXOMA VIRUS

CROSS-REFERENCE

This application claims the benefit of U.S. Provisional Application No. 62/697,581, filed Jul. 13, 2018, which application is incorporated herein by reference.

STATEMENT AS TO FEDERALLY SPONSORED RESEARCH

This invention was made with government support under P50 CA186781 awarded by the National Institutes of Health. The government has certain rights in the invention.

BACKGROUND OF THE DISCLOSURE

Current treatments used to treat various types of cancer tend to work by poisoning or killing the cancerous cell. Unfortunately, treatments that are toxic to cancer cells typically tend to be toxic to healthy cells as well. Moreover, the heterogenous nature of tumors is one of the primary reasons that effective treatments for cancer remain elusive. Current mainstream therapies such as chemotherapy and radiotherapy tend to be used within a narrow therapeutic window of toxicity. These types of therapies are considered blunt tools that have limited applicability due to the varying types of tumor cells and the limited window in which these treatments can be administered.

SUMMARY OF THE DISCLOSURE

Disclosed herein, in certain embodiments, are methods of inhibiting or treating a cancer with use of a myxoma virus (MYXV) engineered to express TNF protein. In some embodiments, also described herein is a method of inhibiting or treating a cancer with use of a mononuclear peripheral blood cells and/or a bone marrow cells treated with a TNF expressing myxoma virus. In additional embodiments, described herein comprise engineered myxoma virus and pharmaceutical compositions for use with one or more of the methods described herein.

Disclosed herein, in certain embodiments, is a myxoma virus (MYXV) engineered to express a tumor necrosis factor (TNF) protein, wherein the MYXV comprises a modification at or adjacent to one or more genes associated with rabbit cell tropism. In some embodiments, the TNF protein is a TNF alpha protein. In some embodiments, the TNF protein is a surface TNF protein. In some embodiments, the TNF protein is a soluble TNF protein. In some embodiments, the TNF protein is a human TNF protein. In some embodiments, one or more genes associated with rabbit cell tropism comprises M11L, M063, M135R, M136R, M-T2, M-T4, M-T5, or M-T7. In some embodiments, the MYXV comprises a partial deletion or full deletion of M135R gene. In some embodiments, the MYXV comprises a modification of M135R gene that impairs the function of M135R gene. In some embodiments, the TNF protein replaces the M135R gene within the MYXV genome. In some embodiments, the TNF protein is inserted between M135R gene and M136R gene within the MYXV genome. In some embodiments, the MYXV further comprises a fluorescent protein. In some embodiments, the MYXV is Lausanne strain. In some embodiments, the MYXV is vMyx-M135KO-hTNF. In some embodiments, the MYXV is vMyx-hTNF-M135-136.

Disclosed herein, in certain embodiments, is a pharmaceutical composition comprising a myxoma virus described herein, and a pharmaceutically acceptable excipient. In some embodiments, the pharmaceutical composition is formulated for systemic administration. In some embodiments, the pharmaceutical composition is formulated for local administration. In some embodiments, the pharmaceutical composition is formulated for parenteral administration.

Disclosed herein, in certain embodiments, is a composition comprising peripheral blood mononuclear cells (PBMCs), bone marrow (BM) cells, or a combination thereof treated ex vivo by a myxoma virus (MYXV) engineered to express a tumor necrosis factor (TNF) protein. In some embodiments, the MYXV is a myxoma virus described herein. In some embodiments, the MYXV is vMYX-SODKO-hTNF. In some embodiments, the PBMCs, BM cells, or a combination thereof comprise autologous cells. In some embodiments, the PBMCs, BM cells, or a combination thereof are obtained from heterologous donors.

Disclosed herein, in certain embodiments, is a method of inhibiting or treating a cancer in a subject in need thereof, comprising administering to the subject a myxoma virus (MYXV) engineered to express a tumor necrosis factor (TNF) protein. In some embodiments, the MYXV is a myxoma virus described herein. In some embodiments, the MYXV is vMYX-SODKO-hTNF. In some embodiments, the cancer is a solid tumor. In some embodiments, the cancer has metastasized to a second location in the subject. In some embodiments, the second location comprises a lung, a brain, a liver and/or a lymph node of the subject. In some embodiments, the cancer comprises osteosarcoma, triple negative breast cancer, or melanoma. In some embodiments, the method further comprises administering to the subject an additional therapeutic agent. In some embodiments, the additional therapeutic agent is an immune checkpoint modulator. In some embodiments, the additional therapeutic agent is administered to the subject prior to administering the MYXV or the composition. In some embodiments, the additional therapeutic agent is administered to the subject after administering the MYXV or the composition. In some embodiments, the additional therapeutic agent is administered to the subject as a combination with the MYXV or the composition. In some embodiments, the subject is a human. In some embodiments, the method further comprises selecting a subject that has or is suspected of having a cancer. In some embodiments, the myxoma virus is capable of infecting cells that have a deficient innate anti-viral response. In some embodiments, cells that have a deficient innate anti-viral response comprise cancer cells. In some embodiments, cells infected with the myxoma virus express TNF.

Disclosed herein, in certain embodiments, is a method of inhibiting or treating a cancer in a subject in need thereof, comprising administering to the subject a composition described herein. In some embodiments, the method further comprises adsorbing the myxoma virus ex vivo onto the surface of the PBMCs, BM cells, or a combination thereof. In some embodiments, adsorbing the myxoma virus onto the surface of the PBMCs, BM cells, or a combination thereof comprises exposing the PBMCs, BM cells, or a combination thereof to the myxoma virus under a condition that permit binding of the myxoma virus to the surface of the PBMCs, BM cells, or a combination thereof. In some embodiments, the condition comprises a temperature of from about 4° C. to about 37° C. In some embodiments, the condition comprises a temperature of from about 20° C. to about 37° C., from about 20° C. to about 28° C., from about 24° C. to about 26° C., from about 30° C. to about 37° C., or from about 35° C. to about 37° C. In some embodiments, the condition comprises an incubation time of at least 5 minutes, 10 minutes, 15 minutes, 20 minutes, 30 minutes, 1 hour, 1.5 hour, 2 hours, 3 hours, 4 hours, 6 hours, 8 hours, 10 hours, 12 hours, or more. In some embodiments, the PBMCs, BM cells, or a combination thereof are obtained from the subject or an HLA-related donor. In some embodiments, the virus-adsorbed PBMCs, BM cells, or a combination thereof are administered to the subject systemically. In some embodiments, the cancer is a solid tumor. In some embodiments, the cancer has metastasized to a second location in the subject. In some embodiments, the second location comprises a lung, a brain, a liver and/or a lymph node of the subject. In some embodiments, the cancer comprises osteosarcoma, triple negative breast cancer, or melanoma. In some embodiments, the method further comprises administering to the subject an additional therapeutic agent. In some embodiments, the additional therapeutic agent is an immune checkpoint modulator. In some embodiments, the additional therapeutic agent is administered to the subject prior to administering the MYXV or the composition. In some embodiments, the additional therapeutic agent is administered to the subject after administering the MYXV or the composition. In some embodiments, the additional therapeutic agent is administered to the subject as a combination with the MYXV or the composition. In some embodiments, the subject is a human. In some embodiments, the method further comprises selecting a subject that has or is suspected of having a cancer. In some embodiments, the myxoma virus is capable of infecting cells that have a deficient innate anti-viral response. In some embodiments, cells that have a deficient innate anti-viral response comprise cancer cells. In some embodiments, cells infected with the myxoma virus express TNF.

Disclosed herein, in certain embodiments, is a kit comprising a myxoma virus described herein, a pharmaceutical composition described herein, or a composition described herein.

BRIEF DESCRIPTION OF THE DRAWINGS

The novel features of certain embodiments of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 2A and FIG. 2B show genetic maps of two exemplary different engineered MYXV. FIG. 2A shows a genetic map of the vMyx-135KO-hTNF insertion plasmid and summary of the genetic map of the recombinant myxoma virus. Note this virus has a knockout of the viral M135R gene. FIG. 2B shows a genetic map of the vMyx-hTNF-(M135-136) insertion plasmid and summary of construction of this recombinant myxoma virus. Note that this virus has a wild-type MYXV backbone, because the TNF transgene is inserted at an intergenic locus between the viral M135R and M136R genes, and thus has no gene knockout. Each plasmid was used for transfection of RK-13 cells prior to infection with the parental wild-type vMyx-Lau for the construction of the vMyx-M135KO-hTNF (FIG. 2A) and vMyx-hTNF-(M135-136) (FIG. 2B) viruses, respectively.

FIG. 6 is a graph showing ex vivo vMyx-SODKO-hTNF loaded PBMCs dose response survival. Balb/c mice treated with progressively increasing doses of Balb/c PBMC loaded vMyx-SODKO-hTNF survive significantly longer than untreated controls. Animals were inoculated with $2\times10^6$ K7M2-luc cells at day 0 and were treated with ex vivo PBMCs that had been infected with respective MYXV construct for one hour prior to treatment. Animals were then monitored for disease progression until euthanization criteria were met.

FIG. 13 shows testing of vMyx-SODKO-hTNF delivered via ex vivo-loaded syngeneic murine bone marrow leukocytes to eliminate pre-seeded murine multiple myeloma in immunocompetent mice. FIG. 13A shows in vivo data using bortezomib-resistant VK*12598 myeloma cells transplanted into C57/Bl mice, where they migrate mostly to the bone marrow and spleen. Survival curves were generated 100 days post cancer implantation (FIG. 13B). FIG. 13C corresponds to the percentages of survival.

FIG. 14 shows combination therapy with vMyx-hTNF-(M135-M136) pre-loaded ex vivo on BM leukocytes with either SMAC Mimetic or Immune Checkpoint Inhibitor. Combination therapy was tested with the SMAC mimetic compound LCL161 (50 mg/Kg), or the checkpoint inhibitor monoclonal antibody (mAb) α-muPD-1, combined with vMyx-hTNF-(M135-M136) delivered via ex vivo-preloaded autologous murine bone marrow leukocytes (FIG. 14A). FIG. 14B shows in vivo data including the survival curves. FIG. 14C describes the percentages of survival.

DETAILED DESCRIPTION OF THE DISCLOSURE

Certain Terminologies

Figure 1:
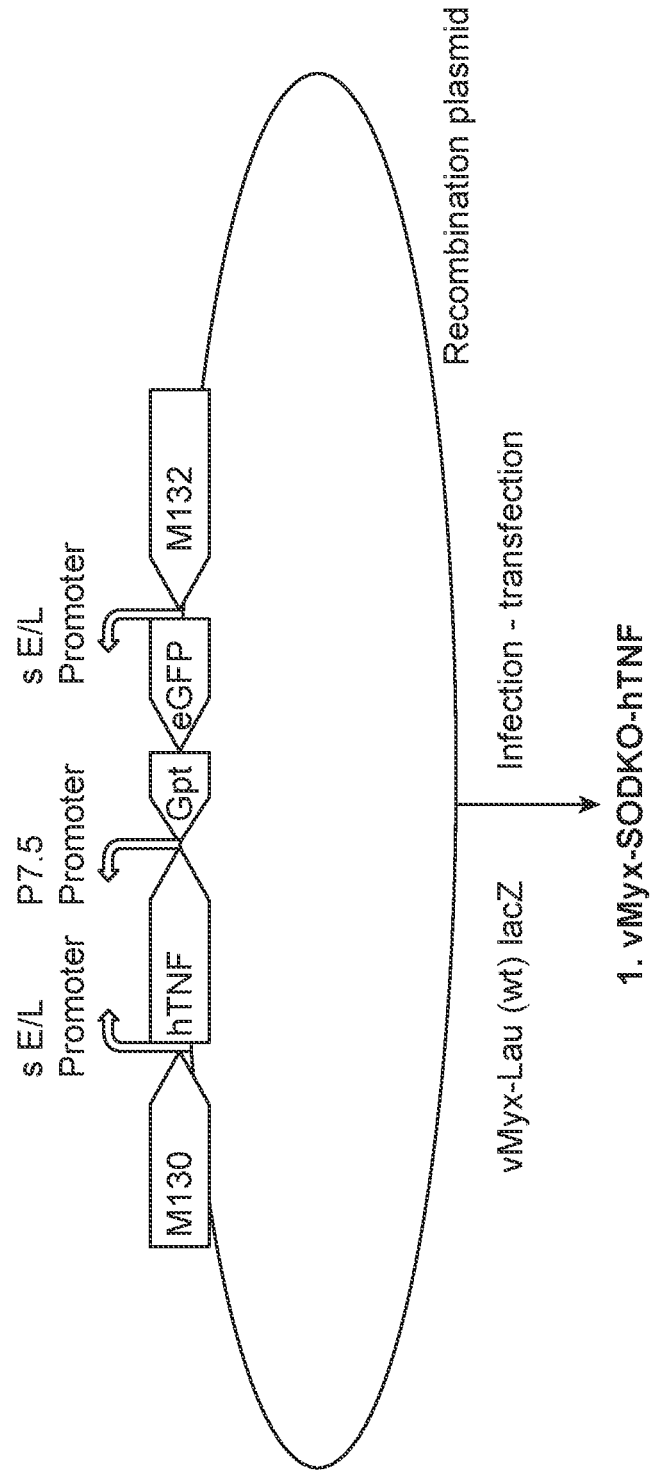
FIG. 1 shows a genetic map of the vMyx-SODKO-hTNF insertion plasmid and summary of construction of virus. This plasmid was used for transfection of RK-13 cells prior to infection with vMyx-LacZ virus for the construction of the vMyx-SODKO-hTNF virus.

Unless otherwise noted, technical terms are used according to conventional usage. Definitions of common terms in molecular biology may be found in Benjamin Lewin, Genes V, published by Oxford University Press, 1994 (ISBN 0-19-854287-9); Kendrew et al. (eds.), The Encyclopedia of Molecular Biology, published by Blackwell Science Ltd., 1994 (ISBN 0-632-02182-9); and Robert A. Meyers (ed.), Molecular Biology and Biotechnology: a Comprehensive Desk Reference, published by VCR Publishers, Inc., 1995 (ISBN 1-56081-569-8).

Unless otherwise explained, all technical and scientific terms used herein have the same meaning as commonly understood by one of ordinary skill in the art to which this disclosure belongs. Although methods and materials similar or equivalent to those described herein can be used in the practice or testing of this disclosure, suitable methods and materials are described below. In addition, the materials, methods, and examples are illustrative only and not intended to be limiting.

Reference in the specification to "some embodiments", "an embodiment", "one embodiment" or "other embodiments" means that a particular feature, structure, or characteristic described in connection with the embodiments is included in at least some embodiments, but not necessarily all embodiments, of the inventions.

The section headings used herein are for organizational purposes only and are not to be construed as limiting the subject matter described.

The following explanations of terms and methods are provided to better describe the present compounds, compositions and methods, and to guide those of ordinary skill in the art in the practice of the present disclosure. It is also to be understood that the terminology used in the disclosure is for the purpose of describing particular embodiments and examples only and is not intended to be limiting.

As used herein, the singular forms "a," "an," and "the" are intended to include the plural forms as well, unless the context clearly indicates otherwise.

As used herein, ranges and amounts can be expressed as "about" a particular value or range. About also includes the exact amount. Hence "about 5 µL" means "about 5 µL" and also "5 µL." Generally, the term "about" includes an amount that would be expected to be within experimental error.

As used herein, the term "and/or" refers to and encompasses any and all possible combinations of one or more of the associated listed items, as well as the lack of combinations when interpreted in the alternative ("or").

As used herein, "one or more" or at least one can mean one, two, three, four, five, six, seven, eight, nine, ten or more, up to any number.

As used herein, the term "comprises" means "includes." Hence "comprising A or B" means including A, B, or A and B.

An "effective amount" or "therapeutically effective amount" refers to an amount of a compound or composition of this invention that is sufficient to produce a desired effect, which can be a therapeutic and/or beneficial effect. The effective amount will vary with the age, general condition of the subject, the severity of the condition being treated, the particular agent administered, the duration of the treatment, the nature of any concurrent treatment, the pharmaceutically acceptable carrier used, and like factors within the knowledge and expertise of those skilled in the art. As appropriate, an effective amount or therapeutically effective amount in any individual case can be determined by one of ordinary skill in the art by reference to the pertinent texts and literature and/or by using routine experimentation. (See, for example, Remington, The Science and Practice of Pharmacy (latest edition)).

As used herein, the term "subject" and "patient" are used interchangeably herein and refer to both human and nonhuman animals. The term "nonhuman animals" of the disclosure includes all vertebrates, e.g., mammals and non-mammals, such as nonhuman primates, sheep, dog, cat, horse, cow, rodents (e.g., mice, rats, etc.) and the like. Preferably, the subject is a human patient. In particular embodiments, the subject of this disclosure is a human subject.

The term "a cell" as used herein includes a single cell as well as a plurality or population of cells. Administering or exposing an agent to a cell includes both in vitro and in vivo administrations.

A "subject in need thereof" or "a subject in need of" is a subject known to have, or is suspected of having a cancer, such as a solid tumor.

As used herein, the term "cancer" refers to a malignant neoplasm that has undergone characteristic anaplasia with loss of differentiation, increased rate of growth, invasion of surrounding tissue, and is capable of metastasis.

Residual cancer is cancer that remains in a subject after any form of treatment given to the subject to reduce or eradicate cancer. Metastatic cancer is a cancer at one or more sites in the body, e.g., a second site, other than the site of origin of the original (primary) cancer from which the metastatic cancer is derived. Local recurrence is reoccurrence of the cancer at or near the same site (such as in the same tissue) as the original cancer.

Examples of solid cancers, such as sarcomas and carcinomas, include fibrosarcoma, myxosarcoma, liposarcoma, chondrosarcoma, osteosarcoma, osteogenic sarcoma, and other sarcomas, synovioma, mesothelioma, Ewing's sarcoma, leiomyosarcoma, rhabdomyosarcoma, colon carcinoma, lymphoid malignancy, pancreatic cancer, breast cancer, lung cancers, non-small cell lung cancer, ovarian cancer, prostate cancer, hepatocellular carcinoma, squamous cell carcinoma, basal cell carcinoma, adenocarcinoma, sweat gland carcinoma, sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, bladder carcinoma, and CNS tumors (such as a glioma, astrocytoma, medulloblastoma, craniopharyogioma, ependymoma, pinealoma, hemangioblastoma, acoustic neuroma, oligodendroglioma, menangioma, melanoma, neuroblastoma and retinoblastoma).

Examples of hematologic cancers include myeloma, lymphoma, and leukemia. In some instances, exemplary hematologic cancers include B-cell or T-cell hematologic cancers. In some cases, exemplary hematologic cancers include Hodgkin's lymphoma or non-Hodgkin's lymphoma.

As used herein, the term "chemotherapeutic agent" refers to any chemical agent with therapeutic usefulness in the treatment of diseases characterized by abnormal cell growth. Such diseases include tumors, neoplasms, and cancer, as well as diseases characterized by hyperplastic growth such as psoriasis. In one embodiment, a chemotherapeutic agent is an agent of use in treating cancer, such as an antineoplastic agent. In one embodiment, a chemotherapeutic agent is a radioactive compound. One of skill in the art can readily identify a chemotherapeutic agent of use (see for example, Slapak and Kufe, *Principles of Cancer Therapy*, Chapter 86 in *Harrison's Principles of Internal Medicine*, 14th edition; Perry et al., *Chemotherapy*, Ch. 17 in Abeloff, *Clinical Oncology* 2nd ed., 2000 Churchill Livingstone, Inc; Baltzer and Berkery. (eds): *Oncology Pocket Guide to Chemotherapy*, 2nd ed. St. Louis, Mosby-Year Book, 1995; Fischer Knobf, and Durivage (eds): *The Cancer Chemotherapy Handbook*, 4th ed. St. Louis, Mosby-Year Book, 1993. Combination chemotherapy is the administration of more than one agent to treat cancer. Such as a myxoma virus expressing TNF and one or more other chemotherapeutic agents, which can be administered simultaneously or separated in time in any order.

As used herein, the term "inhibiting or treating a disease," such as cancer, refers to inhibiting the full development of a disease or condition. "Treatment" refers to a therapeutic intervention that ameliorates a sign or symptom of a disease or pathological condition after it has begun to develop. The term "ameliorating," with reference to a disease or pathological condition, refers to any observable beneficial effect of the treatment. The beneficial effect can be evidenced, for example, by a delayed onset of clinical symptoms of the disease in a susceptible subject, a reduction in severity of some or all clinical symptoms of the disease, a slower progression of the disease, such a metastasis, an improvement in the overall health or well-being of the subject, or by other parameters well known in the art that are specific to the particular disease. A "prophylactic" treatment is a treatment administered to a subject who does not exhibit signs of a disease or exhibits only early signs for the purpose of decreasing the risk of developing pathology, for example metastatic cancer.

As used herein the "pharmaceutically acceptable carriers" useful in conjunction with therapeutic compounds disclosed herein are conventional. *Remington's Pharmaceutical Sciences*, by E. W. Martin, Mack Publishing Co., Easton, Pa., 19th Edition (1995), describes compositions and formulations suitable for pharmaceutical delivery of therapeutic agents.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

As used herein, the terms "pharmaceutical" and "therapeutic agent" refer to a chemical compound or a composition capable of inducing a desired therapeutic or prophylactic effect when properly administered to a subject or a cell.

As used herein, the term "tumor" refers to the product of neoplasia, which is an abnormal growth of tissue that results from excessive cell division. A tumor that invades the surrounding tissue and/or can metastasize is referred to as "malignant." Neoplasia is one example of a proliferative disorder.

The term "replication-competent" as used herein refers to a virus that is capable of infecting and replicating within a particular host cell.

INTRODUCTION

Cancers that metastasize to the lungs, and other organs, represent a major challenge in both basic and clinical cancer research. The ability to treat lung metastases to date has been challenging, with cancers such as osteosarcoma, melanoma, and breast cancer all having 5-year survival rates of under 25% with current therapies. Current treatment paradigms are a mix of classic radiotherapies, chemotherapies and targeted therapies, but there is no one treatment that is effective for all tumors. One therapy that was once touted as a potential "magic bullet" for cancer treatment is Tumor Necrosis Factor (TNF). Since its first discovery by William Coley over a century ago, and molecular characterization decades later, TNF has been shown to be a tantalizing, but enigmatic anti-cancer reagent and immune regulator. Studies of its use in both locally treated in distally isolated tumors and as a systemic treatment have revealed severe toxicities and low anti-tumor response rates. Indeed, some studies also found that systemic administration of TNF alone could even promote tumor growth in certain cancers.

TNF (also referred to as TNFα, cachexin, or cachectin) is a cytokine that is an integral part of the inflammatory immune response (Coley, W B. 2015 The treatment of malignant tumors by repeated inoculations of erysipelas: with a report of ten original cases. Am. J. Med. Sci. 105, 487-511 (1893)). It is expressed primarily as a cell surface immune ligand, but TNF can be secreted as a soluble cytokine when expressed in cells that express the converting enzymes that catalyze cleavage and release of the soluble ligand, for example cells of the myeloid lineage. One TNF effector pathway that has been documented is the induction of cellular death through the TNF Receptor-1 (TNFR1) pathway, leading to apoptosis or necroptosis depending on downstream effects within specific target cells (Moriwaki K, Bertin J, Gough P, Orlowski G, Chan F K. 2016. Differential roles of RIPK1 and RIPK3 in TNF-induced necroptosis and chemotherapeutic agent-induced cell death. Cell death & disease 6:e1636). TNF is also an activator of the innate and adaptive immune responses, for example by activating anti-tumor CD8+ T cells and NK cells (Kashii, Y, Giorda, R, Herberman, R. B., Whiteside, T. L. Vujanovic, N. L. Constitutive expression and role of the TNF family ligands in apoptotic killing of tumor cells by human NK cells. J. Immunol. 163, 5358-5366; Prevost-Blondel, A, Roth, E., Rosenthal, F. Pircher, H. 2000 Crucial role of TNF-α in CD8 cell-mediated elimination of 3LL-A9 Lewis lung carcinoma cells in vivo. J. Immunol. 164, 3645-3651). TNF was originally thought of as a potential anti-tumor wonder drug. Although preliminary experiments with systemic injections of TNF in mice seemed to back up this optimism, the transition from the lab to the clinic showed that TNF was not only an activator of the immune system, but it also caused severe systemic toxicities in patients treated systemically with the soluble ligand. Studies also showed that this systemic TNF treatment did not induce comparable anti-tumor effects in patients that had been observed in murine models (Balkwill, F. Tumor necrosis factor and cancer. 2009 Nature Reviews Cancer 9, 361).

Oncolytic virotherapy has re-emerged as a viable treatment strategy (Russell S J, Peng K-W, Bell J C. 2012. Oncolytic virotherapy. Nature biotechnology 30:658-670). Although exploiting oncolytic virotherapy to treat cancer as an idea dates back over a century, it has only been in the past two decades that it has become a progressively more feasible modality for the treatment of human tumors refractory to standard therapies (Kelly E, Russell S J. 2007. History of oncolytic viruses: genesis to genetic engineering. Molecular Therapy 15:651-659).

Oncolytic viruses are mammalian viruses that are designed and/or selected for their ability to selectively infect and kill transformed cancer cells, and by their ability to activate the host immune system against not only the virus, but also tumor antigens (Lichty B D, Breitbach C J, Stojdl D F, Bell J C. 2014. Going viral with cancer immunotherapy. Nature Reviews Cancer 14:559-567). Myxoma virus (MYXV) is a member of the family poxviridae and genus leporipoxvirus (Chan W M, Rahman M M, McFadden G. 2013. Oncolytic Myxoma virus: the path to clinic. Vaccine 31:4252-4258; Chan W M, McFadden G. 2014. Oncolytic poxviruses. Annual review of virology 1:191-214). In nature, MYXV is rabbit-specific and does not cause infection or disease in humans or mice. However, because of the nature of cancer pathway mutations associated with carcinogenesis, most if not all cancer cells from both mice and humans invariably lose elements of their innate ability to resist infection by many viruses, including MYXV (Chan W M, McFadden G. 2014. Oncolytic poxviruses. Annual review of virology 1:191-214; Sypula J, Wang F, Ma Y, Bell J, McFadden G. 2004. Myxoma virus tropism in human tumor cells. Gene Ther Mol Biol 8:103-114). Another feature of the biology in this system is the large and genetically stable poxvirus genome that allows for the genetic manipulation with multiple therapeutic transgenes (Nayerossadat N, Maedeh T, Ali P A. 2012. Viral and nonviral delivery systems for gene delivery. Advanced biomedical research 1). As disclosed herein MYXV genes that regulate different forms of immune modulation and/or cell death is optionally ablated and therapeutic anti-cancer transgenes is introduced to induce increase immunogenicity and/or induce preferred forms of cancer cell death.

Engineered Myxoma Virus and Methods of Use

In certain embodiments, disclosed herein comprises engineered myxoma virus that encodes an exogenous TNF protein. In some instances, the myxoma virus comprises a modification at or adjacent to one or more genes associated with rabbit cell tropism. In some instances, the one or more genes associated with rabbit cell tropism comprises M11L, M063, M135R, M136R, M-T2, M-T4, M-T5, or M-T7. In some instances, the one or more genes associated with rabbit cell tropism comprise M135R, M136R, or a combination thereof.

In some instances, disclosed herein comprises an engineered myxoma virus (MYXV) that is engineered to express a TNF protein, in which the MYXV comprises a modification of M135R gene. In some instances, the modification is a deletion that impairs the function of a protein encoded by the M135R gene. In some cases, the modification is a partial deletion (e.g., a 10%, 20%, 30%, 40%, 50%, 60%, 70%, 80%, 90%, or 95% deletion) of the M135R gene. In other cases, the modification is a full deletion of the M135R gene. In additional cases, the modification is a replacement of the M135R gene with the TNF protein. In further cases, the engineered MYXV is vMyx-M135KO-hTNF. In still further cases, the engineered MYXV is vMyx-M135KO-hTNF as illustrated in FIG. 2A.

Figure 2B:
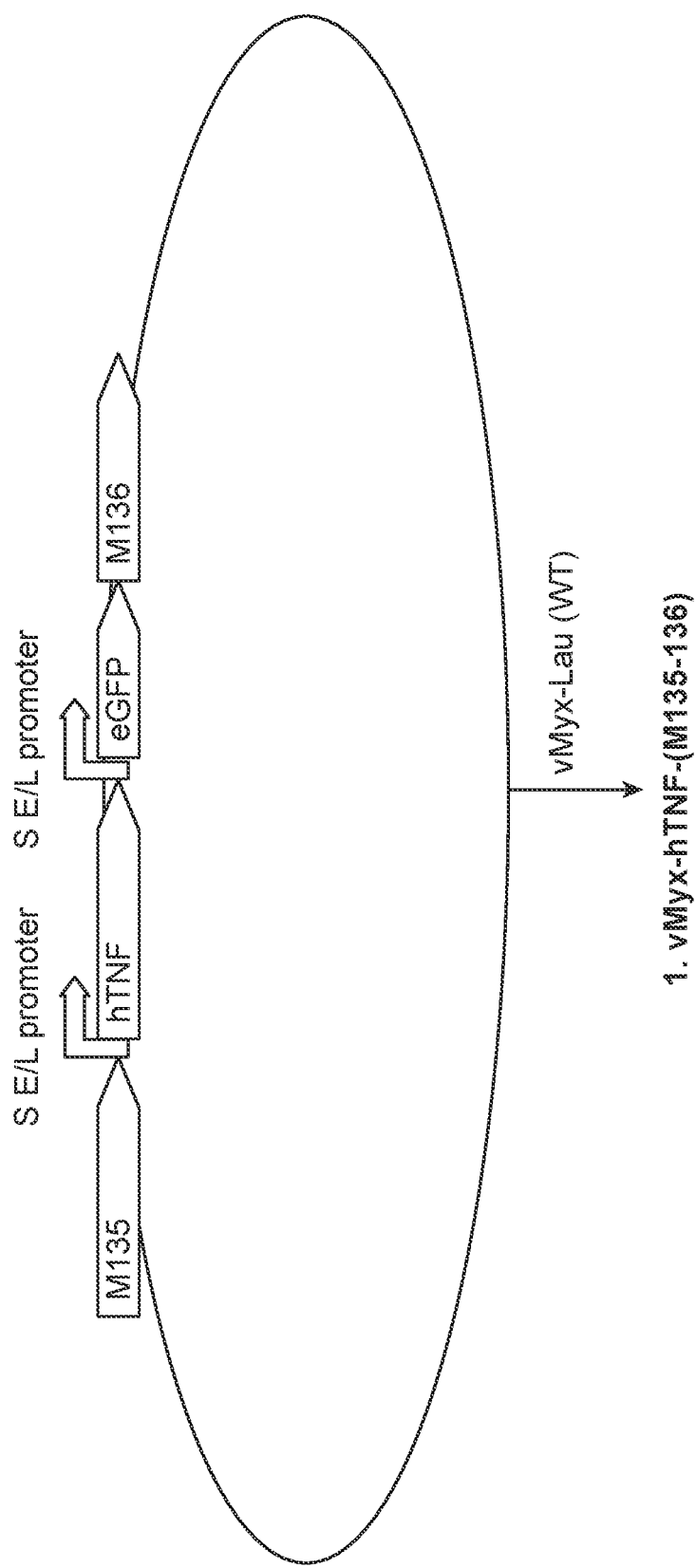

In some instances, disclosed herein comprises an engineered myxoma virus (MYXV) that is engineered to express a TNF protein, in which the TNF protein is inserted between M135R gene and M136R gene within the MYXV genome. In some instances, the engineered MYXV is vMyx-hTNF-M135-136. In some instances, the engineered MYXV is vMyx-hTNF-M135-136 as illustrated in FIG. 2B.

In some instances, the TNF protein comprises at least 90%, 95%, 96%, 97%, 98%, or 99% such as between 95% and 98%, 95% and 99%, including 90%, 91%, 92%, 93%, 94%, 95%, 96%, 97%, 98%, 99% sequence identity or comprises the sequence as illustrated in UniProtKB-P01375, which is published on 3 Jul. 2019 (Entry version 247) and is herein incorporated by reference. In some instances, the TNF protein is a soluble TNF comprising at least 90%, 95%, 96%, 97%, 98%, or 99%, such as between 95% and 98%, 95% and 99%, including 90%, 91%, 92%, 93%, 94%, 95%, 96%, 97%, 98%, 99% sequence identity to residues 77-233 of UniProtKB-P01375. In some cases, the soluble TNF comprises residues 77-233 of UniProtKB-P01375.

In some cases, the engineered MYXV comprising the TNF protein further comprises a fluorescent protein. Exemplary fluorescent proteins include blue/UV proteins such as TagBFP, Azurite, Sims, or Sapphire; cyan proteins such as ECFP, cerulean, or mTurquoise; green proteins such as green fluorescent protein (GFP), Emerald, mUKG, mWasabi, or Clover; yellow proteins such as EYFP, citrine, venus, or SYFP2; orange proteins such as monomeric Kusabira-Orange, mKO2, or mOrange; red proteins such as mRaspberrym mCherry, mStrawberry, mTangerine, tdTomato, mApple, or mRuby; photoactivatible proteins such as PA-GFP, PAmCherryl, or PATagRFP; and photoswitchable proteins such as Dropna.

In certain embodiments, also described herein is a method of cancer treatment that uses induced TNF expression (e.g., a transmembrane TNF protein or a soluble TNF protein) in combination with the oncolytic Myxoma virus (MYXV). As discussed above, secreted TNF has been shown to be an anti-tumor molecule, but that is not amenable to systemic use due to its small therapeutic window and severe side effects. Furthermore, oncolytic MYXV has been shown to be a tumor specific anti-tumor agent with a broad tropism for a wide variety of tumor types. In some cases, disclosed herein are MYXV that are modified to express hTNF, e.g., at the virus-infected tumor cell surface, i.e. on the surface of infected cells; or as a secreted version. To achieve effects disclosed herein the oncolytic MYXV can be engineered to express human TNF from recombinant MYXV constructs (generically called vMyx-hTNF) as an immune ligand that is expressed in virus-infected cells under a strong virus specific promoter. The advantage of MYXV-based expression of TNF is that the ligand is expressed only in the virus-infected tumor tissues, and at low amounts that obviate the severe side effects observed in systemic delivery of the soluble TNF ligand.

In some instances, the Myxoma virus genome is readily modified to express one or more therapeutic transgenes using standard molecular biology techniques known to a skilled person, and described for example in Sambrook et al. ((2001) Molecular Cloning: a Laboratory Manual, 3rd ed., Cold Spring Harbour Laboratory Press). A skilled person will be able to readily determine which portions of the Myxoma viral genome can be deleted such that the virus is still capable of productive infection, for example to provide a replication competent virus. For example, non-essential regions of the viral genome that can be deleted can be deduced from comparing the published viral genome sequence with the genomes of other well-characterized viruses (see for example C. Cameron, S. Hota-Mitchell, L. Chen, J. Barrett, J.-X. Cao, C. Macaulay, D. Willer, D. Evans, and G. McFadden, Virology (1999) 264: 298-318)). Thus, aspects of the present disclosure concern a method for inhibiting and/or treating cancer in a subject in need thereof. In certain embodiments, the method includes administering to a subject, such as a human subject, a MYXV that expresses tumor necrosis factor (TNF) (e.g., a transmembrane TNF protein or a soluble TNF protein), thereby treating and/or inhibiting the cancer in the subject in need thereof. In certain embodiments, the MYXV comprises vMyx-M135KO-hTNF. In certain embodiments, the MYXV comprises vMyx-hTNF-M135-136. In certain embodiments, the MYXV comprises vMYX-SODKO-hTNF. In certain embodiments, the subject is a human subject. In certain embodiments, the method further includes selecting a subject, such as a human subject, that has or is suspected of having cancer. In certain embodiments, the MYXV is administered systemically. In certain embodiments, the MYXV is administered at the site of a tumor and/or metastasis. MYXV has been shown to infect cells that have a deficient innate anti-viral response. Having "a deficient innate anti-viral response" as used herein refers to a cell that, when exposed to a virus or when invaded by a virus, does not induce anti-viral defense mechanisms, which include inhibition of viral replication, production of interferon, induction of the interferon response pathway, and apoptosis. The term includes a cell, such as a cancer cell, that has a reduced or defective innate anti-viral response upon exposure to or infection by a virus as compared to a normal cell, for example, a non-infected, or non-cancer cell. This includes a cell that is non-responsive to interferon and a cell that has a reduced or defective apoptotic response or induction of the apoptotic pathway. The deficiency may be caused by various causes, including infection, genetic defect, or environmental stress. It will however be understood that when the deficiency is caused by a pre-existing infection, superinfection by MYXV may be excluded and a skilled person can readily identify such instances. A skilled person can readily determine without undue experimentation whether any given cell type has a deficient innate anti-viral response and therefore infective by MYXV. Thus, in certain embodiments of the method, the MYXV is capable of infecting cells that have a deficient innate anti-viral response. In one embodiment, the cells are non-responsive to interferon. In specific embodiments, the cell is a mammalian cancer cell. In one embodiment, the cell is a human cancer cell including a human solid tumor cell.

The MYXV may be any virus that belongs to the Leporipoxvirus species of pox viruses that is replication-competent. The MYXV may be a wild-type strain of MYXV or it may be a genetically modified strain of MYXV. In some instances, the MYXV is Lausanne strain. In some instances, the MYXV is a South American MYXV strain that circulates in *Sylvilagus brasiliensis*. In some instances, the MYXV is a Californian MYXV strain that circulates in *Sylvilagus bachmani*. In some instances, the MYXV is 6918, an attenuated Spanish field strain that comprises modifications in genes M009L, M036L, M135R, and M148R (GenBank Accession number EU552530 which is hereby incorporated by reference as provided by GenBank on Jul. 11, 2019). In some instances, the MYXV is 6918VP60-T2 (GenBank Accession Number EU552531 which is hereby incorporated by reference as provided by GenBank on Jul. 11, 2019). In some instances, the MYXV is a strain termed the Standard laboratory Strain (SLS).

In some instances, the MYXV comprises at least 90%, 95%, or 99% sequence identity to a sequence disclosed in Cameron, et al., "The complete DNA sequence of Myxoma Virus," Virology 264: 298-318 (1999) (which is herein incorporated by reference in its entirety). In some cases, the MYXV comprises the sequence disclosed in Cameron, et al., "The complete DNA sequence of Myxoma Virus," Virology 264: 298-318 (1999).

In certain embodiments, the cells that have a deficient innate anti-viral response comprise cancer cells. In certain embodiments, the cells infected with the MYXV express TNF. In some instances, the TNF is expressed on the surface. In some cases, the TNF is a soluble TNF. As disclosed herein, the efficacy results demonstrated against lung metastases are, by extension, applicable to other solid cancers, both primary and metastatic. TNF can be both a powerful killer of cancerous cells, and also an activator of the innate and adaptive immune responses against tumor cells. The application of this virus to a broad spectrum of tumor types, based on what is known about the biology of the virus and TNF, provides for an ideal candidate for the treatment of diverse cancer types. A cancer may be diagnosed using criteria generally accepted in the art, including the presence of a malignant tumor.

Types of cancer that may be treated according to the disclosed method include, but are not limited to, solid tumors such as sarcomas and carcinomas include but are not limited to fibrosarcoma, myxosarcoma, liposarcoma, chondrosarcoma, osteosarcoma, osteogenic sarcoma, and other sarcomas, synovioma, mesothelioma, Ewing's sarcoma, leiomyosarcoma, rhabdomyosarcoma, colon carcinoma, lymphoid malignancy, pancreatic cancer, breast cancer, lung cancers, non-small cell lung cancer, ovarian cancer, prostate cancer, hepatocellular carcinoma, squamous cell carcinoma, basal cell carcinoma, adenocarcinoma, sweat gland carcinoma, sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, bladder carcinoma, and CNS tumors (such as a glioma, astrocytoma, medulloblastoma, craniopharyogioma, ependymoma, pinealoma, hemangioblastoma, acoustic neuroma, oligodendroglioma, menangioma, melanoma, neuroblastoma and retinoblastoma). In certain embodiments, the cancer is a solid tumor. In certain embodiments, the cancer has metastasized to a second location in the subject. In certain embodiments, the second location comprises a lung, a brain, a liver and/or a lymph node of the subject. In certain embodiments, the cancer comprises osteosarcoma, triple negative breast cancer, or melanoma.

In some embodiments, the type of cancer further includes hematologic cancers such as Hodgkin's lymphoma or non-Hodgkin's lymphoma.

When administered to a subject, an effective amount of a MYXV expressing TNF, such as cell surface expressed TNF, or a soluble form, is the amount required, at the dosages and for sufficient time period, for the virus to alleviate, improve, mitigate, ameliorate, stabilize, prevent the spread of, slow or delay the progression of or cure the disease, such as cancer, for example a solid tumor that has metastasized to the lungs, brain, liver or any other organ. For example, it may be an amount sufficient to achieve the effect of reducing the number of or destroying cancerous cells or neoplastic cells, or reducing the number of or destroying cells chronically infected with a virus, or inhibiting the growth and/or proliferation of such cells and/or the reduction in the number and/or sites of metastasis.

The effective amount to be administered to a subject can vary depending on many factors such as the pharmacodynamic properties of the MYXV, the modes of administration, the age, health and weight of the subject, the nature and extent of the disease state, the frequency of the treatment and the type of concurrent treatment, if any, and the virulence and titer of the virus.

The MYXV may be administered initially in a suitable amount that may be adjusted as required, depending on the clinical response of the subject. The effective amount of virus can be determined empirically and depends on the maximal amount of the MYXV that can be administered safely, and the minimal amount of the virus that produces the desired result.

MYXV may be administered to the subject using standard methods of administration, in one embodiment, the virus is administered systemically. In another embodiment, the virus is administered by injection at the disease site, In various embodiments, the virus may be administered orally or parenterally, or by any standard method known in the art.

To produce the same clinical effect when administering the virus systemically as that achieved through injection of the virus at the disease site, administration of significantly higher amounts of virus may be required. However, the appropriate dose level should be the minimum amount that would achieve the desired result.

The concentration of virus to be administered will vary depending on the virulence of the particular strain of MYXV that is to be administered and on the nature of the cells that are being targeted. In one embodiment, a dose of less than about $3 \times 10^{10}$ focus forming units ("ffu"), also called "infectious units", is administered to a human subject, in various embodiments, between about $10^2$ to about $10^9$ pfu, between about $10^2$ to about $10^7$ pfu, between about $10^3$ to about $10^6$ pfu, or between about $10^4$ to about $10^5$ pfu may be administered in a single dose.

The MYXV expressing TNF, such as cell surface expressed TNF or a soluble form may be administered as a sole therapy or may be administered in combination with other therapies, including chemotherapy, immunotherapy and/or radiation therapy. For example, the MYXV expressing TNF may be administered either prior to or following surgical removal of a primary tumor or prior to, concurrently with or following treatment such as administration of radiotherapy or conventional chemotherapeutic drugs.

In some embodiments, the immunotherapy comprises an immune modulator. Exemplary immune checkpoint modulators include, but are not limited to, PD-L1 inhibitors such as durvalumab (Imfinzi) from AstraZeneca, atezolizumab (MPDL3280A) from Genentech, avelumab from EMD Serono/Pfizer, CX-072 from CytomX Therapeutics, FAZ053 from Novartis Pharmaceuticals, KN035 from 3D Medicine/Alphamab, LY3300054 from Eli Lilly, or M7824 (anti-PD-L1/TGFbeta trap) from EMD Serono; PD-L2 inhibitors such as GlaxoSmithKline's AMP-224 (Amplimmune), and rHIgM12B7; PD-1 inhibitors such as nivolumab (Opdivo) from Bristol-Myers Squibb, pembrolizumab (Keytruda) from Merck, AGEN 2034 from Agenus, BGB-A317 from BeiGene, Bl-754091 from Boehringer-Ingelheim Pharmaceuticals, CBT-501 (genolimzumab) from CBT Pharmaceuticals, INCSHR1210 from Incyte, JNJ-63723283 from Janssen Research & Development, MEDI0680 from MedImmune, MGA 012 from MacroGenics, PDR001 from Novartis Pharmaceuticals, PF-06801591 from Pfizer, REGN2810 (SAR439684) from Regeneron Pharmaceuticals/Sanofi, or TSR-042 from TESARO; CTLA-4 inhibitors such as ipilimumab (also known as Yervoy®, MDX-010, BMS-734016 and MDX-101) from Bristol Meyers Squibb, tremelimumab (CP-675,206, ticilimumab) from Pfizer, or AGEN 1884 from Agenus; LAG3 inhibitors such as BMS-986016 from Bristol-Myers Squibb, IMP701 from Novartis Pharmaceuticals, LAG525 from Novartis Pharmaceuticals, or REGN3767 from Regeneron Pharmaceuticals; B7-H3 inhibitors such as enoblituzumab (MGA271) from MacroGenics; KIR inhibitors such as Lirilumab (IPH2101; BMS-986015) from Innate Pharma; CD137 inhibitors such as urelumab (BMS-663513, Bristol-Myers Squibb), PF-05082566 (anti-4-1BB, PF-2566, Pfizer), or XmAb-5592 (Xencor); PS inhibitors such as Bavituximab; and inhibitors such as an antibody or fragments (e.g., a monoclonal antibody, a human, humanized, or chimeric antibody) thereof, RNAi molecules, or small molecules to TIM3, CD52, CD30, CD20, CD33, CD27, OX40, GITR, ICOS, BTLA (CD272), CD160, 2B4, LAIR1, TIGHT, LIGHT, DR3, CD226, CD2, or SLAM.

In some embodiments, the MYXV expressing TNF is formulated as an ingredient in a pharmaceutical composition. Therefore, in a further embodiment, there is provided a pharmaceutical composition comprising Myxoma virus expressing TNF and a pharmaceutically acceptable excipient or diluent. The compositions may routinely contain pharmaceutically acceptable concentrations of salt, buffering agents, preservatives and various compatible carriers.

The pharmaceutical compositions may additionally contain additional therapeutic agents, such as additional anti-cancer agents. In one embodiment, the compositions include a chemotherapeutic agent. The chemotherapeutic agent, for example, may be substantially any agent, which exhibits an oncolytic effect against cancer cells or neoplastic cells of the subject and that does not inhibit or diminish the tumor killing effect of the MYXV expressing TNF. For example, the chemotherapeutic agent may be, without limitation, an anthracycline, an alkylating agent, an alkyl sulfonate, an aziridine, an ethylenimine, a methylmelamine, a nitrogen mustard, a nitrosourea, an antibiotic, an antimetabolite, a folic acid analogue, a purine analogue, a pyrimidine analogue, an enzyme, a podophyllotoxin, a platinum-containing agent or a cytokine. Preferably, the chemotherapeutic agent is one that is known to be effective against the particular cell type that is cancerous or neoplastic.

In some cases, the additional therapeutic agent comprises an immune checkpoint modulator, as such those described above.

The proportion and identity of the pharmaceutically acceptable excipient or diluent is determined by chosen route of administration, compatibility with a live virus and standard pharmaceutical practice. Generally, the pharmaceutical composition will be formulated with components that will not significantly impair the biological properties of the MYXV expressing TNF. The pharmaceutical composition can be prepared by known methods for the preparation of pharmaceutically acceptable compositions suitable for administration to subjects, such that an effective quantity of the active substance or substances is combined in a mixture with a pharmaceutically acceptable vehicle. Suitable vehicles are described, for example, in Remington's Pharmaceutical Sciences (Remington's Pharmaceutical Sciences, Mack Publishing Company, Easton, Pa., USA 1995). On this basis, the compositions include, albeit not exclusively, solutions of the MYXV expressing TNF in association with one or more pharmaceutically acceptable excipient, vehicles, or diluents, and contained in buffer solutions with a suitable pH and iso-osmotic with physiological fluids.

The pharmaceutical composition may be administered to a subject in a variety of forms depending on the selected route of administration, as will be understood by those skilled in the art. In some instances, the pharmaceutical composition is administered systemically. In other instances, the pharmaceutical composition is administered locally. In some cases, the pharmaceutical composition is administered orally. In additional cases, the pharmaceutical composition is administered parenterally. Parenteral administration includes intravenous, intraperitoneal, subcutaneous, intramuscular, transepithelial, nasal, intrapulmonary, intrathecal, rectal and topical modes of administration. Parenteral administration may be by continuous infusion over a selected period of time.

The pharmaceutical composition may be administered orally, for example, with an inert diluent or with a carrier, or it may be enclosed in hard or soft shell gelatin capsules, or it may be compressed into tablets. For oral therapeutic administration, the MYXV expressing TNF may be incorporated with an excipient and be used in the form of ingestible tablets, buccal tablets, troches, capsules, elixirs, suspensions, syrups, wafers and the like.

Solutions of MYXV expressing TNF may be prepared in a physiologically suitable buffer. Under ordinary conditions of storage and use, these preparations contain a preservative to prevent the growth of microorganisms, but that will not inactivate the live virus. A person skilled in the art would know how to prepare suitable formulations. Conventional procedures and ingredients for the selection and preparation of suitable formulations are described, for example, in Remington's Pharmaceutical Sciences and in The United States Pharmacopeia: The National Formulary (USP 24 NF19) published in 1999. The dose of the pharmaceutical composition that is to be used depends on the particular condition being treated, the severity of the condition, the individual subject parameters including age, physical condition, size and weight, the duration of the treatment, the nature of concurrent therapy (if any), the specific route of administration and other similar factors that are within the knowledge and expertise of the health practitioner. In certain embodiments, the therapeutic virus may be freeze dried for storage at room temperature.

The MYXV expressing TNF or pharmaceutical compositions comprising the MYXV expressing TNF may also be packaged as a kit, containing instructions for use of Myxoma virus expressing TNF to treat cancer.

In addition to expression of TNF, the MYXV can be modified to carry any other gene that will enhance the anticancer effect of the MYXV treatment. Such a gene may be a gene that is involved in triggering apoptosis, or is involved in targeting the infected cell for immune destruction, such as a gene that repairs a lack of response to interferon, or that results in the expression of a cell surface marker that stimulates an antibody response, such as a bacterial cell surface antigen. The MYXV may also be modified to express genes involved in shutting off the neoplastic or cancer cell's proliferation and growth, thereby preventing the cells from dividing. As well, the virus may be modified to include therapeutic genes, such as genes involved in the synthesis of chemotherapeutic agents, or it may be modified to have increased replication levels in cells of the particular species from which the cells to be inhibited or killed are derived, for example, human cells.

As discussed above, MYXV is capable of selectively infecting cells that have a deficient innate anti-viral response, and can be used as an indicator of such a deficiency in cells. Thus, cells removed from a subject may be assayed for deficiency in innate anti-viral response using the methods of the present invention. Such determination may indicate, when combined with other indicators, that the subject may be suffering from a particular disease state, for example, cancer. The cells may be removed from a subject, including a human subject, using known biopsy methods. The biopsy method will depend on the location and type of cell that is to be tested. Cells are cultured according to known culturing techniques, and are exposed to MYXV, by adding live MYXV, to the culture medium. The multiplicity of infection ("MOI), may be varied to determine an optimum MOI for a given cell type, density and culture technique, using a positive control cell culture that is known to be infected upon exposure to MYXV.

The amount of MYXV added to the cultured cells may be varied depending on cell type, method of culturing and strain of virus. Such parameters can be readily tested and adjusted with minimal testing using routine methods.

Infectivity of the cultured cells by MYXV, may be determined by various methods known to a skilled person, including the ability of the MYXV to cause cell death. It may also involve the addition of reagents to the cell culture to complete an enzymatic or chemical reaction with a viral expression product. The viral expression product may be expressed from a reporter gene that has been inserted into the MYXV genome.

In one embodiment, the MYXV may be modified to enhance the ease of detection of infection state. For example, the MYXV may be genetically modified to express a marker that can be readily detected by phase contrast microscopy, fluorescence microscopy or by radioimaging. The marker may be an expressed fluorescent protein or an expressed enzyme that may be involved in a colorimetric or radiolabeling reaction. In another embodiment, the marker may be a gene product that interrupts or inhibits a particular function of the cells being tested.

The MYXV may be prepared using standard techniques known in the art. For example, the virus may be prepared by infecting cultured rabbit cells, or immortalized permissive human or primate cells, with the MYXV strain that is to be used, allowing the infection to progress such that the virus replicates in the cultured cells and can be released by standard methods known in the art for disrupting the cell surface and thereby releasing the virus particles for harvesting. Once harvested, the virus titer may be determined by infecting a confluent lawn of rabbit cells and performing a plaque assay (see Mossman et al. (1996) Virology 215:17-30 which is hereby incorporated by reference in its entirety).

Further disclosed is a delivery strategy where the therapeutic MYXV virus is first adsorbed ex vivo to mixed leukocytes from either bone marrow or peripheral blood mononuclear cells prior to infusion, such as re-infusion back, into the cancer patient. In this strategy, MYXV expressing human TNF is delivered to metastatic cancer sites via migration of leukocytes pre-infected with virus ex vivo. This systemic delivery method is sometimes called "ex vivo virotherapy", or EVV (aka EV2), because the virus is first delivered to isolated leukocytes prior to infusion into the patient. The MYXV construct and this novel delivery strategy has shown the ability to significantly reduce tumor burden and increase survival in a murine lung metastases model (see Example 1). As disclosed herein, the administration of myxoma virus (MYXV) constructs that express cell surface human TNF effectively delivered the MYXV virus to sites of metastatic lung disease via virus-bearing "carrier" cells. Furthermore, as disclosed herein, the inventors have demonstrated that this cell-assisted delivery of TNF-expressing virus (generically designated as vMyx-hTNF) has the ability to reduce tumor burden and increase survival of mice with lung metastases (see Example 1). These results demonstrate that the cell-mediated delivery of TNF-expressing MYXV increases the level of direct killing of target lung metastatic tumor cells, but (while not being bound by theory) acts as an activator of the host immune system, which can lead to long term regression of cancer. This provides a new method of treatment of solid cancers that have metastasized to the lungs, liver, brain, bone and/or lymph nodes, which has proved to be difficult with current treatments. Thus, in certain embodiments, the method includes administering to a subject mononuclear peripheral blood cells and/or bone marrow cells, wherein the mononuclear peripheral blood cells and/or bone marrow cells include a MYXV that expresses cell surface tumor necrosis factor (TNF), thereby treating and/or inhibiting the cancer in the subject in need thereof. The combined "leukocyte/vMyx-hTNF" therapy causes increased cellular death in the tumor beds to enhance anti-tumor immunogenicity, but produces TNF substantially only in situ in the virus-infected metastatic tumor tissues, such a lung tumor tissues, to limit off-target systemic toxic side effects. The results of tests presented in the Example 1 below in a murine osteosarcoma lung metastases model show that this strategy is effective in reducing tumor burden and increasing median survival time. Furthermore, the leukocyte/vMyx-hTNF strategy represents a new potential therapeutic regimen for all solid cancers, which metastasize, for example, to the lung, irrespective of original tumor type, by selectively expressing cell surface TNF in a cancer tissue restricted manner. While not being bound by theory it is believed that this leukocyte/vMyx-hTNF strategy works synergistically with other established cancer therapies for solid cancers that frequently metastasize, for example, to the lung. In certain embodiments, the method includes adsorbing the MYXV into the surface of the mononuclear peripheral blood cells and/or a bone marrow cells. It is possible that some fraction of the mononuclear peripheral blood cells and/or bone marrow cells are infected; however, it is not likely that this is significant in the method disclosed herein. In certain embodiments, adsorbing the myxoma virus onto the surface of the mononuclear peripheral blood cells and/or bone marrow cells includes exposing the mononuclear peripheral blood cells and/or bone marrow cells to the myxoma virus under conditions that permit binding of the myxoma virus to the surface of the mononuclear peripheral blood cells and/or bone marrow cells.

Aspects of this disclosure is directed to new method for delivering oncolytic MYXV constructs of any kind to metastatic lung disease, namely by pre-loading therapeutic MYXV constructs on mixed leukocytes derived from either bone marrow (BM) or peripheral blood mononuclear cells (PBMCs), such as described above. Such methods can be used to treat any disease state characterized by the presence of cells that have a deficient innate anti-viral response, for example a cancer cell. The MYXV constructs can be modified to include any therapeutic gene or "therapeutic transgenes. The term "therapeutic gene" or "therapeutic transgenes" as used herein is intended to describe broadly any gene the expression of which effects a desired result, for example, anti-cancer effect. For example, the virus may be modified to carry a gene that will enhance the anticancer effect of the viral treatment. Such a gene may be a gene that is involved in triggering apoptosis, or is involved in targeting the infected cell for immune destruction, such as a gene that repairs a lack of response to interferon, or that results in the expression of a cell surface marker that stimulates an antibody response, such as a bacterial cell surface antigen. The virus may also be modified to express genes involved in shutting off the neoplastic or cancer cell's proliferation and growth, thereby preventing the cells from dividing. As well, the virus may be modified to include therapeutic genes, such as genes involved in the synthesis of chemotherapeutic agents, or it may be modified to have increased replication levels in cells of the particular species from which the cells to be inhibited or killed are derived, for example, human cells.

In certain embodiments, the BM or PBMC cells are adsorbed with MYXV constructs for one hour ex vivo, and then the MYXV-loaded leukocytes are infused back into the recipient. In certain embodiments, the mononuclear peripheral blood cells and/or bone marrow cells are obtained from the subject, for example as autologous cells. In other embodiment, the mononuclear peripheral blood cells and/or bone marrow cells are obtained from one or more heterologous donors. Methods of obtaining bone marrow cells and mononuclear peripheral blood cells are known in the art.

Aspects of the present disclosure concern a MYXV that expresses tumor necrosis factor (TNF), e.g., surface TNF or soluble TNF, and kits including the same. In certain embodiments, a MYXV that expresses TNF comprises vMyx-M135KO-hTNF. In certain embodiments, a MYXV that expresses TNF comprises vMyx-hTNF-M135-136. The Myxoma virus expressing TNF or pharmaceutical compositions comprising the MYXV expressing TNF may also be packaged as a kit, containing instructions for use of MYXV expressing TNF to inhibit a cell that has a deficient immune response to treat a cancer.

EXAMPLES

These examples are provided for illustrative purposes only and not to limit the scope of the claims provided herein.

Example 1

Figure 3:
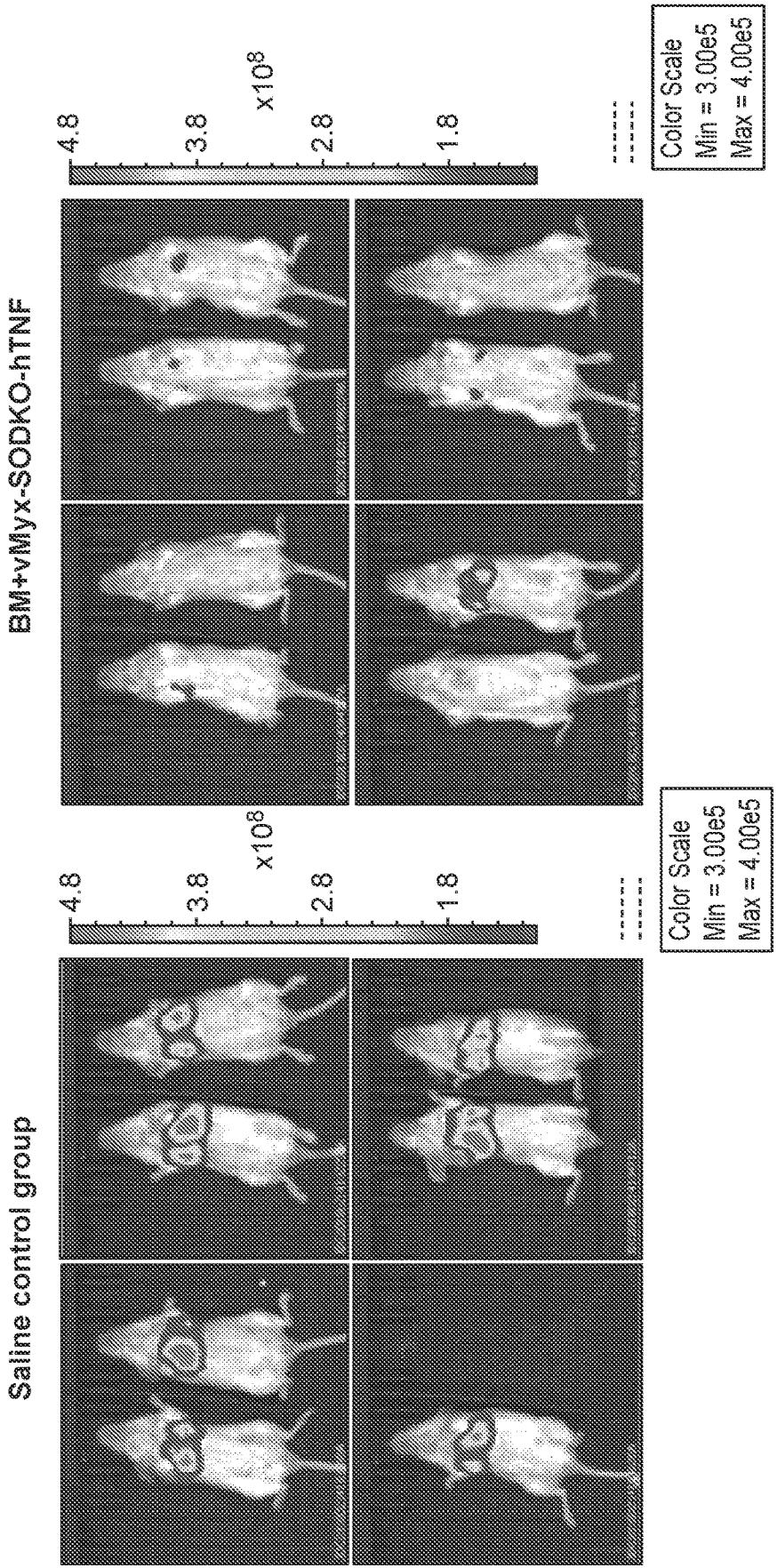
FIG. 3 is a set of images of Balb/c mice 2 weeks post K7M2-Luc tumor inoculation. Untreated animals show advanced tumor in lungs (left), while vMyx-SODKO-hTNF treated animals show significantly smaller tumors (right). Animals were inoculated with $2\times10^6$ K7M2-luc cells at day 0 and were treated with $4\times10^6$ ex vivo BM that had been infected with vMyx-SODKO-hTNF for one hour prior to treatment. Animals at week 2 were then injected with luciferin IP and imaged using IVIS imagining system. Tumor luminesce was calculated and standardized for all animals.
Figure 4:
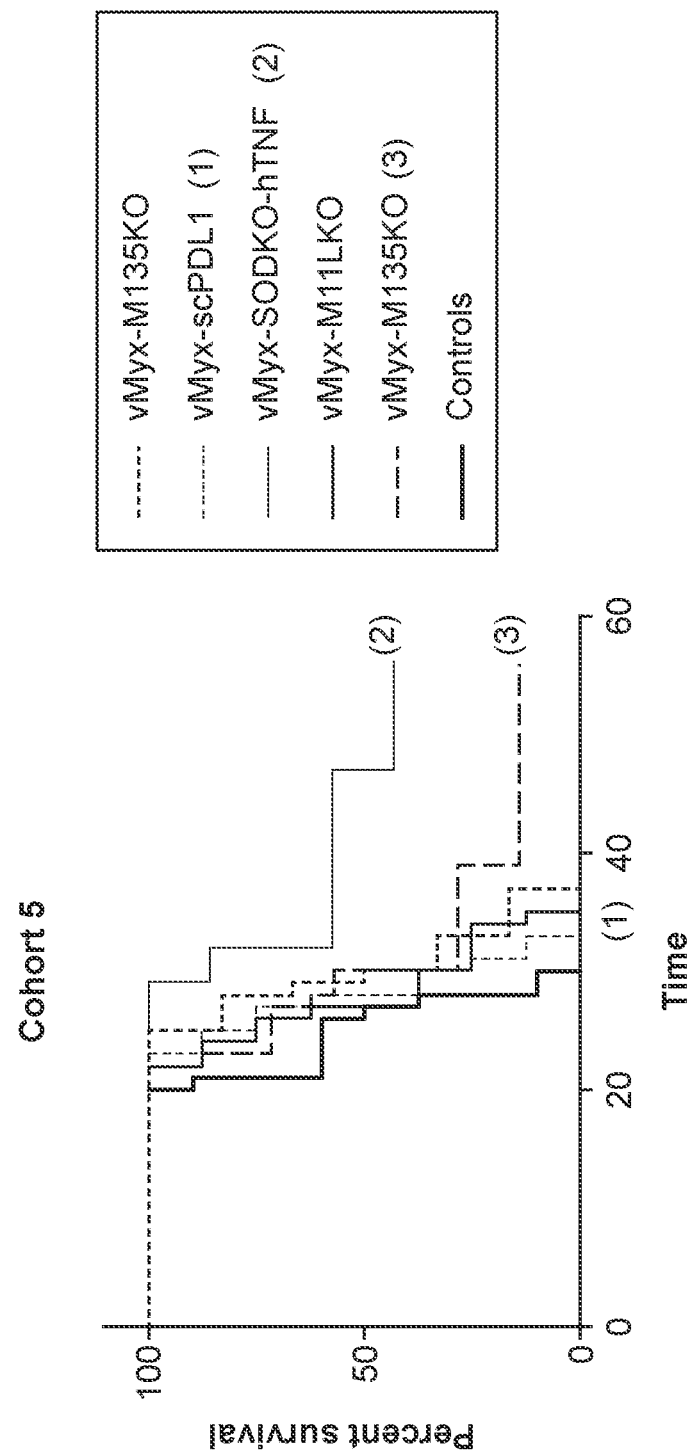
FIG. 4 is a graph showing bone marrow loaded with Myxoma virus (MYXV) expressing hTNF has superior oncolytic ability compared to other MYXV constructs. Kaplan-Meier survival curves show that vMyx-SODKO-hTNF is the only MYXV construct tested to significantly increase mean survival compared to control cohort. Animals were inoculated with $2\times10^6$ K7M2-luc cells at day 0 and were treated with ex vivo bone marrow that had been infected with respective MYXV construct for one hour prior to treatment. Animals were then monitored for disease progression until euthanization criteria were met. At week 8 post inoculation all survivors were euthanized.

This example describes the construction and testing of MYXV expressing TNF.
Design of the Virus The first version of the vMyx-hTNF virus (here called vMyx-SODKO-hTNF) was originally designed and described by Wang et al 2008 (Wang F, Gao X, Barrett J W, Shao Q, Bartee E, Mohamed M R, Rahman M, Werden S, Irvine T, Cao J. Dekaban, G A, McFadden, G. 2008). RIG-I mediates the co-induction of tumor necrosis factor and type I interferon elicited by myxoma virus in primary human macrophages. PLoS pathogens 4:e1000099, which is specifically incorporated herein by reference). In short, the virus was created using the MYXV Lausanne parental strain for purposes that were unrelated to oncolytic virotherapy or for any treatment of cancer. The insertion vector was based on the pBluescript phagemid, and cloned into the 131R ORF (called SOD) along with eGFP, controlled by discrete synthetic vaccinia early late promoters (see map FIG. 1). A second hTNF-expressing virus (called vMyx-M135KO-hTNF) was generated based on the M135R-gene knockout virus platform that is the standard attenuated genetic background for oncolytic MYXV constructs that are being developed for human clinical trials. The strategy for the M135R knockout construction is described in full by Bartee et al 2009 (Bartee E, Mohamed M R, Lopez M C, Baker H V, McFadden G. 2009. The addition of tumor necrosis factor plus beta interferon induces a novel synergistic antiviral state against poxviruses in primary human fibroblasts. Journal of virology 83:498-511 and Barrett J W, Sypula J, Wang F, Alston L R, Shao Z, Gao X, Irvine T S, McFadden G. 2007 M135R Is a Novel Cell Surface Virulence Factor of Myxoma Virus. Journal of Virology. 81(1):106-114, both of which are specifically incorporated herein by reference in their entirety). Briefly, this vMyx-M135KO-hTNF virus was generated using the Multisite gateway three fragment cloning procedure. Element 1 contained 3' fragment of the M134 ORF along with eGFP controlled by the synthetic early/late promoter. Element 2 contained the full hTNF coding sequence also under the control of the synthetic early/late promoter. Finally, element 3 contained a fragment of the 5' M136 gene. These three fragments were combined into a single-entry vehicle plasmid that were used to insert the eGFP-hTNF tandem cassette into the M135R locus in any MYXV genome backbone. This was then used for transfection/infection and recombinant virus was purified using at least 3 rounds of plaque purification (final plasmid used for transfection shown in FIG. 2A).
Animal Studies The efficacy of the vMyx-SODKO-hTNF virus, delivered via leukocytes that had been pre-loaded with virus ex vivo, against lung metastatic osteosarcoma was confirmed using the syngeneic murine osteosarcoma model in immunocompetent Balb/c mice. Animals were inoculated via lateral tail vein with $2\times10^6$ K7M2-FLuc murine osteosarcoma cells on day zero. Four days post inoculation, bone marrow (BM) from control Balb/c mice was harvested, counted, and infected with virus at an MOI (Multiplicity of Infection) of 2-10 infectious virus units per nucleated cell. Cells and virus were allowed to adsorb for 1 hour at 37 C. Ex vivo virus loaded BM was then injected retro-orbitally at $4\times10^6$ cells per animal. Animals were then imaged using an IVIS in vivo imaging system for luciferase luminescence weekly starting day 7 post tumor inoculation as a real time measurement of tumor burden, most of which was observed in the recipient lungs. Animals were monitored until they reached predetermined clinical symptoms of progressive disease or until 8 weeks post infection, whichever came first. Results show that animals treated with all the tested virus constructs, with the notable exception of the vMyx-SODKO-hTNF construct, exhibited tumor burdens comparable to controls. With the possible exception of the vMyx-M135KO virus that induced a single longer term survivor, the other test viruses also did not show mean survival that was statistically distinguishable from controls. The vMyx-SODKO-hTNF construct cohort, in contrast, had tumors that were statistically smaller, as measured by luminescence from the tumor cells, than both controls and other constructs at all imaging time points (FIG. 3). The vMyx-SODKO-hTNF also nearly doubled mean survival times compared to controls (FIG. 4), and only in this cohort a significant number of animals that were apparently free of demonstrable tumor burden was observed.

Figure 5:
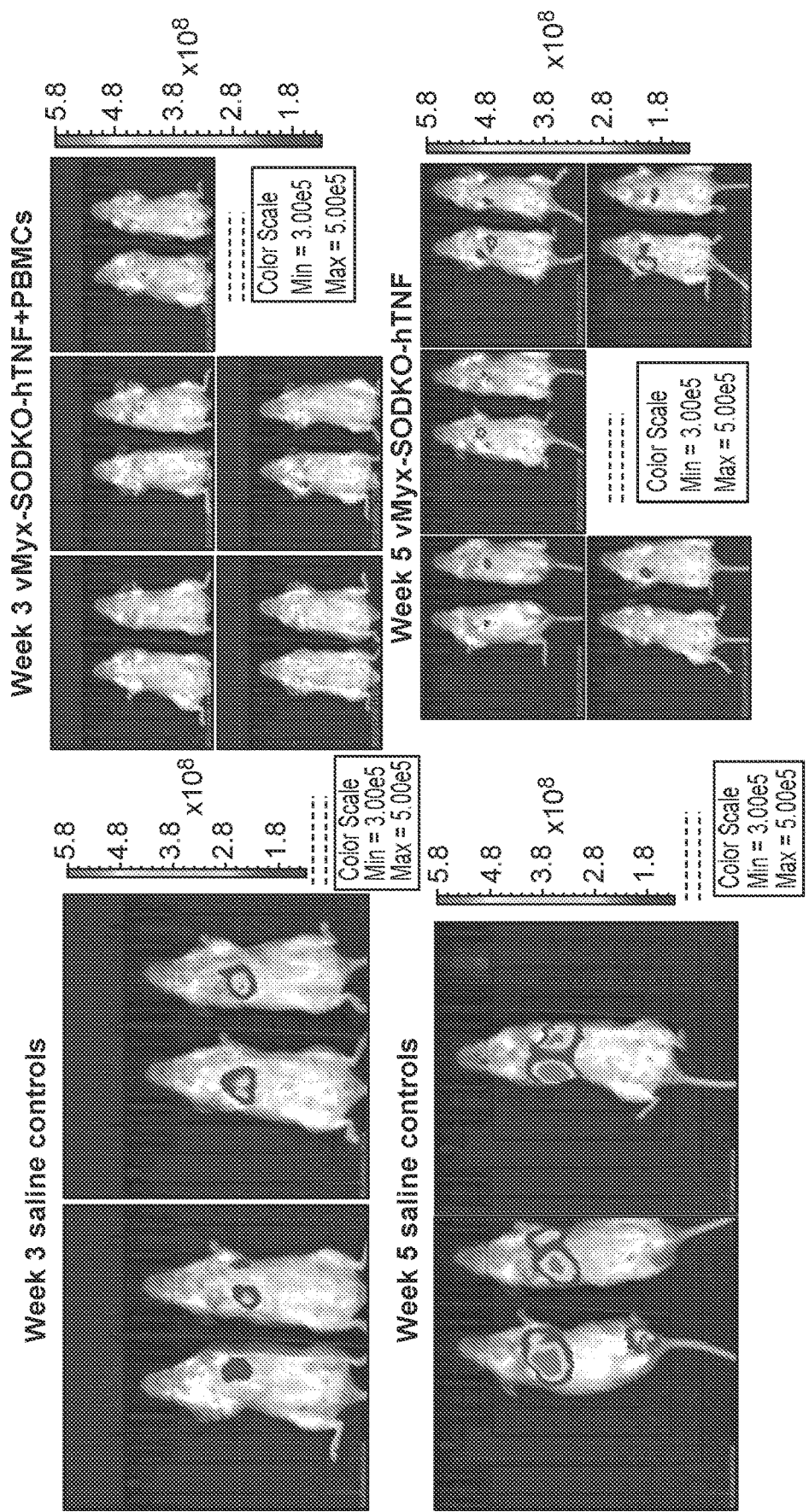
FIG. 5 is two sets of images taken 2 weeks apart showing differences in progression of tumors between untreated controls (left images) and animals treated with vMyx-SODKO-hTNF virus (right images). Animals were inoculated with $2\times10^6$ K7M2-luc cells at day 0 and were treated with $4\times10^6$ ex vivo PBMCs that had been infected with vMyx-SODKO-hTNF for one hour prior to treatment. Animals at week 3 and week 5 were then injected with luciferin IP and imaged using IVIS imagining system. Tumor luminesce was calculated and standardized for all animals.
Figure 7:
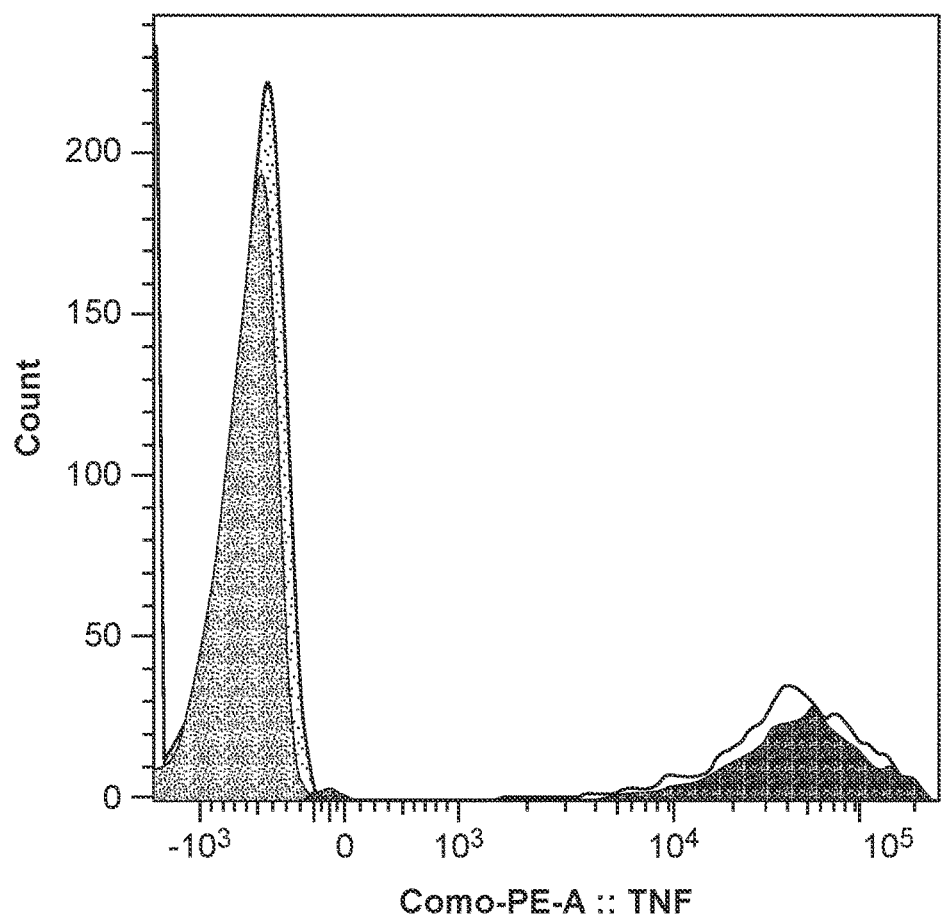
FIG. 7 is a set of flow cytometry data showing that cells infected with vMyx-SODKO-hTNF express hTNF at the cell surface (grey and green) 48 hpi, while control cells are negative for hTNF (pink and purple). Cells were experimentally infected with vMyx-SODKO-hTNF for 48 hours. At 48 hpi cells were lifted using non-enzymatic disassociation buffer and counted. Cells were then stained using mouse anti-human hTNF PE conjugated antibodies and were analyzed using a flow cytometer.

Following these results, BM leukocytes as virus "carrier cells" was compared to exploiting bulk PBMCs as carrier cells for the delivery of therapeutic MYXV constructs to the metastatic lung tumor sites. It was reasoned that PBMCs was a more clinically relevant source of carrier leukocytes for most solid cancers. Animals were inoculated with K7M2-Fluc cells as described above. Four days after tumor inoculation, PBMCs from control Balb/c mice were harvested, and adsorbed with vMyx-SODKO-hTNF (MOI=2) ex vivo for one hour, as described above. Animals were then divided into three dose groups, $1\times10^6$, $2\times10^6$, and $4\times10^6$ PBMCs (each pre-adsorbed with an identical MOI of input virus) and were injected with the respected PBMC/virus doses. Animals were then imaged starting day 7. Results of luciferase imaging showed animals responded to treatment in a dose dependent manner, with animals at the $1\times10^6$ dose responding the least, and animals $4\times10^6$ showing the most significant reduction in tumor luminescence compared to control animals (FIG. 5 and FIG. 6).
Confirmation of TNF Expression in Cells Infected with vMyx-SODKO-hTNF To confirm expression of hTNF by the vMyxv-SODKO-hTNF construct, permissive RK-13 cells were experimentally infected with virus at an MOI of 10. Infection was allowed to progress for 48 hours post infection, and then cells were collected using a non-enzymatic cell disassociation buffer to ensure integrity of membrane bound proteins. Cells were then stained using a mouse anti-human TNF antibody conjugated to PE fluorophore for flow cytometry under nonpermeabilizing conditions that stain only molecules expressed on the cell surface. Cells were then run against uninfected stained controls and uninfected unstained controls. The results of this assay confirmed that at 48 hours post infection there was TNF expressed on the surface of the vMYX-SODKO-hTNF infected cells and no sign of TNF expression by uninfected control cells (FIG. 7). No secreted TNF was detected by Western blotting (not shown), indicating that the infected cells did not express the necessary converting/cleaving enzyme(s) that could in theory produce the secreted form of TNF.

Cell Death Assay In Vitro

Figure 8:
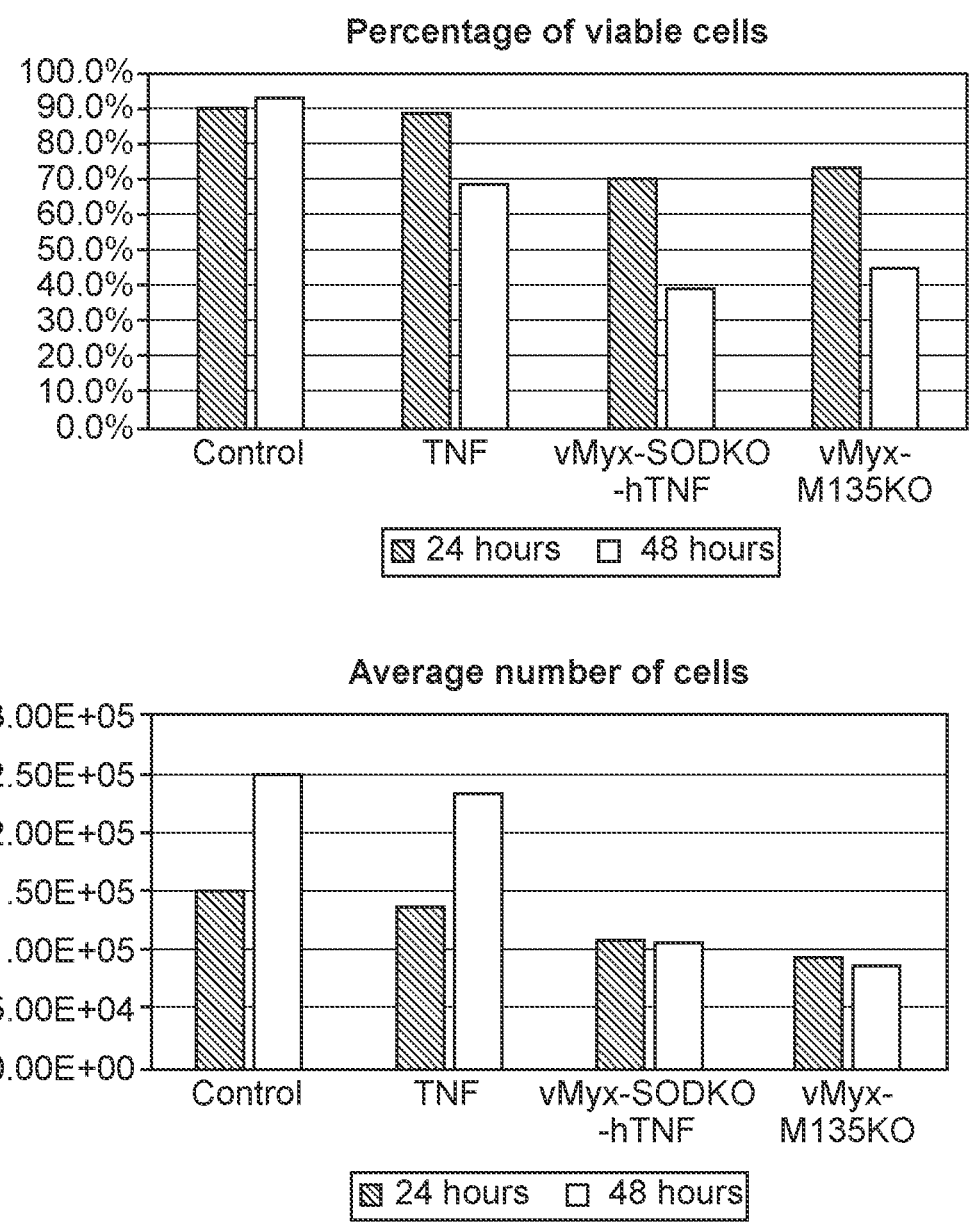
FIG. 8 is a set of graphs of a cell death assay with SYTOX orange confirming that TNF expression from vMyx-SODKO-hTNF does not cause increased cell death in K7M2-luc osteosarcoma cell line compared to control vMyx-M135KO virus that does not express hTNF. Cells were either experimentally infected with vMyx-M135KO virus, or vMyx-SODKO-hTNF virus, or were treated with TNF. Cells were then allowed to incubate for 24 and 48 hours post infection and post treatment. Cells were then stained with SYTOX orange and counted for percentage of fluorescent cells. Average number of cells in each well was also counted for each time point and treatment.

To better understand the mechanism(s) that cause the improved survival and reduced tumor burden observed in tumor bearing animals receiving leukocyte/vMyxv-hTNF virotherapy, a cell death assay was performed to measure the responses of the osteosarcoma cells to different test viruses. This was to determine if the reduced tumor burden was driven by increased direct tumor cell death caused by the TNF expressed by the virus. K7M2-FLuc cells were assayed using flow cytometry for their cell surface expression of TNFR1 and TNFR2. These cells were shown to be positive for expression of both TNFR1 and TNFR2, meaning that it was possible that TNF might directly interact with its cognate receptors on the tumor cells and cause TNF-induced cell death. To confirm if these cells can be killed directly by TNF, they were experimentally grown and were either infected by either vMyx-M135KO, vMyx-SODKO-hTNF or were incubated with purified murine TNF. Cells were then measured for viability using SYTOX orange, which enters and stains cells only after loss of cell membrane integrity associated with various forms of cell death. At 24 or 48 hours post infection/inoculation, cells were incubated with SYTOX orange for 10 minutes, lifted using trypsin, and the cells and supernatant were combined together, centrifuged to wash excess SYTOX. Cells were then resuspended in 100 microliters of DMEM and read using cell counter. The results of this assay showed that murine TNF caused only an increase of 20% cell death compared to controls by 48 hours but at 24 hours post-TNF there was no significant difference. Conversely, vMyx-SODKO-hTNF infection reduced viability by 20% at 24 hours compared to controls, and 50% at 48. This reduction in cell viability is essentially the same as observed after infection with the control vMyx-135KO virus that does not express hTNF. This shows that these osteosarcoma cells are not additionally sensitive to killing by the hTNF, and the increased tumor reduction observed in the animal studies was likely caused by an immune-related mechanism independent of virus-expressed TNF interaction directly with TNFR1 or TNFR2 on the osteosarcoma cells (FIG. 8).

Example 2

This example describes the determination of the efficacy of the vMyx-M135KO-hTNF virus, delivered via leukocytes that had been pre-loaded with virus ex vivo, against triple negative breast cancer.

A syngeneic murine triple negative breast cancer in immunocompetent Balb/c mice is used. Animals are inoculated via lateral tail vein with triple negative breast cancer cells on day zero. Post inoculation, bone marrow (BM) from control Balb/c mice is harvested, counted, and infected with vMyx-M135KO-hTNF and/or control virus. Cells and virus are allowed to adsorb for 1 hour at 37 C. Ex vivo virus loaded BM is then injected retro-orbitally. Animals are then imaged using an IVIS in vivo imaging system for luciferase luminescence weekly post tumor inoculation as a real time measurement of tumor burden, most of which is observed in the recipient lungs. Animals are monitored until they reached predetermined clinical symptoms of progressive disease.

Example 3

This example describes the determination of the efficacy of the vMyx-M135KO-hTNF virus, delivered via leukocytes that had been pre-loaded with virus ex vivo, against metastatic melanoma.

A syngeneic murine triple negative breast cancer in immunocompetent Balb/c mice is used. Animals are inoculated via lateral tail vein with metastatic melanoma cells on day zero. Post inoculation, bone marrow (BM) from control Balb/c mice is harvested, counted, and infected with vMyx-M135KO-hTNF and/or control virus. Cells and virus are allowed to adsorb for 1 hour at 37 C. Ex vivo virus loaded BM is then injected retro-orbitally. Animals are then imaged using an IVIS in vivo imaging system for luciferase luminescence weekly post tumor inoculation as a real time measurement of tumor burden, most of which is observed in the recipient lungs. Animals are monitored until they reached predetermined clinical symptoms of progressive disease.

Example 4

Figure 9:
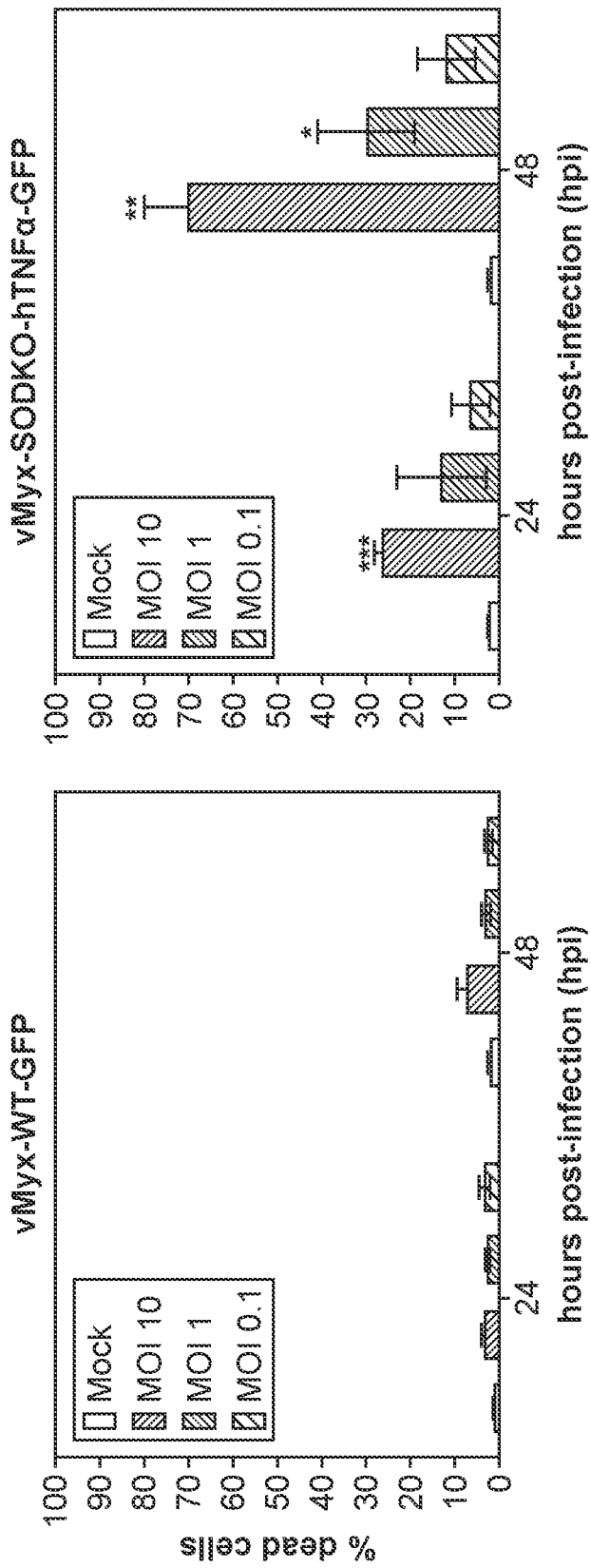
FIG. 9 illustrates quantification of cell death of infected human AML (THP1) cells using flow cytometry. MYXV-mediated total THP1 cell killing was determined from the population of cells that were APC/Cy7+ as defined by gating on cells with Live/Dead staining. Significance (*=p<0.05; =p<0.01; *=p<0.001) was determined using Holm-Sidak's t test for multiple comparisons. The results show that infection of THP-1 cells with vMyx-SODKO-hTNF-GFP caused an overall increase in the number of gated dead cells at the 3 tested multiplicities of infection (MOI=10, 1 or 0.1) at both times post-infection (24 and 48 hrs).

FIG. 9 illustrates quantification of cell death of infected human AML (THP1) cells using flow cytometry. MYXV-mediated total THP1 cell killing was determined from the population of cells that were APC/Cy7$^+$ as defined by gating on cells with Live/Dead staining. Significance (*=p<0.05; =p<0.01; *=p<0.001) was determined using Holm-Sidak's t test for multiple comparisons. The results show that infection of THP-1 cells with vMyx-SODKO-hTNF-GFP caused an overall increase in the number of gated dead cells at the 3 tested multiplicities of infection (MOI=10, 1 or 0.1) at both times post-infection (24 and 48 hrs).

Figure 10:
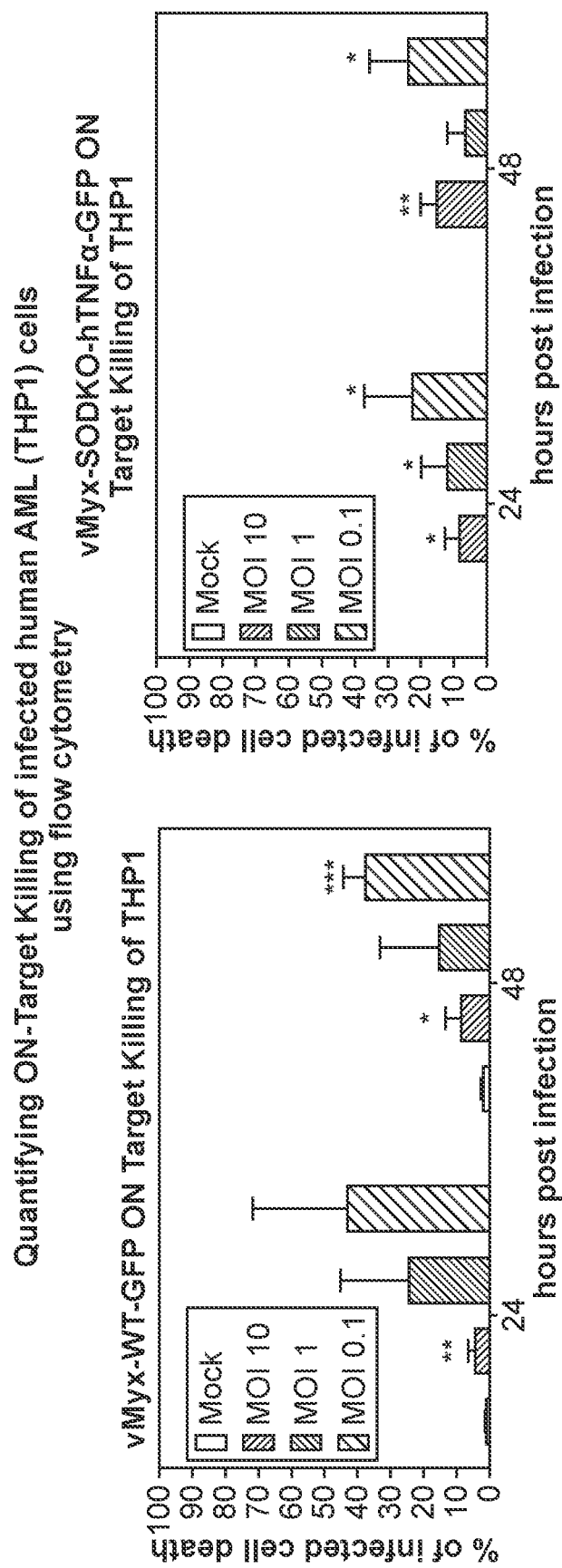
FIG. 10 illustrates quantification of MYXV-mediated ON-Target killing of virus-infected human AML (THP1) cells using flow cytometry. MYXV-mediated "ON-target" killing of THP1 cells was determined from the proportion of cells that were APC/Cy7+, gated from the population of virus-infected cells that were GFP-positive. Significance (*=p<0.05; =p<0.01; *=p<0.001) was determined using Holm-Sidak's t test for multiple comparisons.

FIG. 10 illustrates quantification of MYXV-mediated ON-Target killing of virus-infected human AML (THP1) cells using flow cytometry. MYXV-mediated "ON-target" killing of THP1 cells was determined from the proportion of cells that were APC/Cy7$^+$, gated from the population of virus-infected cells that were GFP-positive. Significance (*=p<0.05; =p<0.01; *=p<0.001) was determined using Holm-Sidak's t test for multiple comparisons. The results show that when THP1 cells were infected with either test virus, the detection of virus-infected dead cells was quite similar for either the control virus or the TNF-expressing construct. This result is in line with the general observation that the capacity of MYXV to kill an infected cell is a consequence largely of the virus platform and is relatively unaffected by most transgenes, including TNF.

Figure 11:
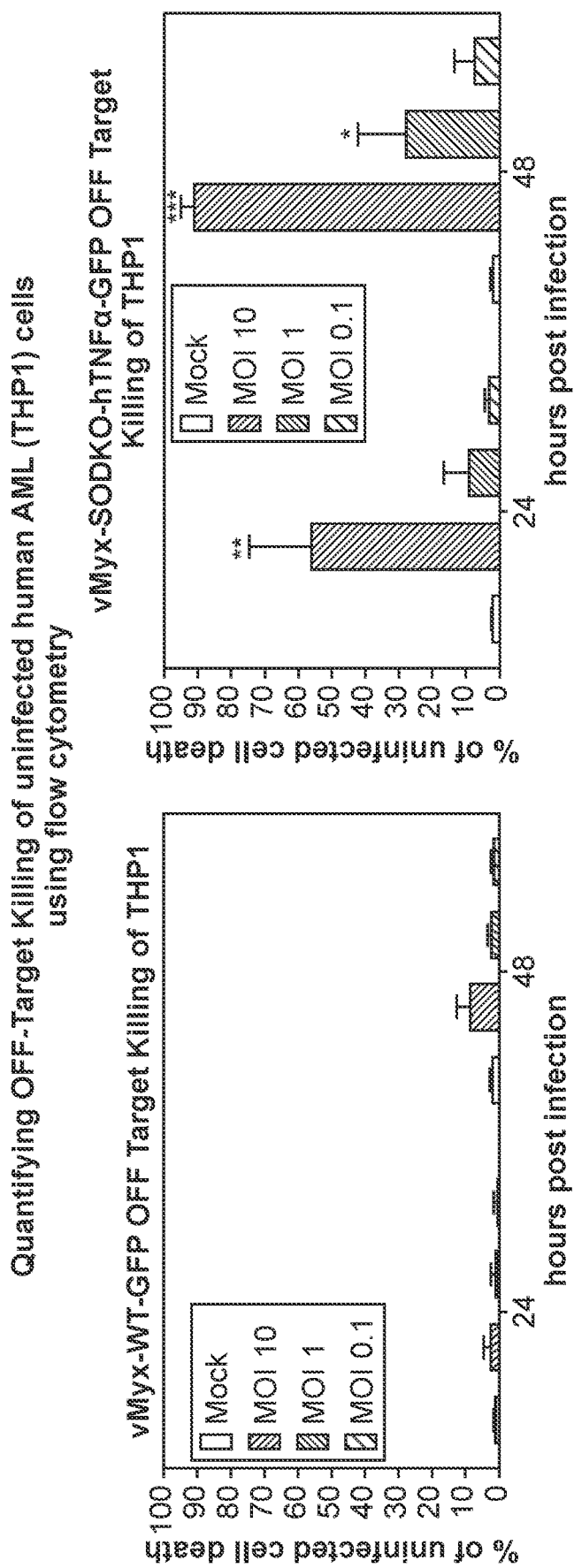
FIG. 11 illustrates quantification of MYXV-induced OFF-Target killing of uninfected human AML (THP1) cells using flow cytometry. MYXV-mediated OFF-Target killing of THP1 cells was determined from the proportion of cells that were APC/Cy7+, gated from the population of cells that were GFP-negative. Significance (*=p<0.05; =p<0.01; *=p<0.001) was determined using Holm-Sidak's t test for multiple comparisons.

FIG. 11 illustrates quantification of MYXV-induced OFF-Target killing of uninfected human AML (THP1) cells using flow cytometry. MYXV-mediated OFF-Target killing of THP1 cells was determined from the proportion of cells that were APC/Cy7$^+$, gated from the population of cells that were GFP-negative. Significance (*=p<0.05; =p<0.01; *=p<0.001) was determined using Holm-Sidak's t test for multiple comparisons. The results show that expression of the hTNF transgene induced considerable killing of uninfected THP1 cells, compared to the unarmed MYXV control infection.

Figure 12:
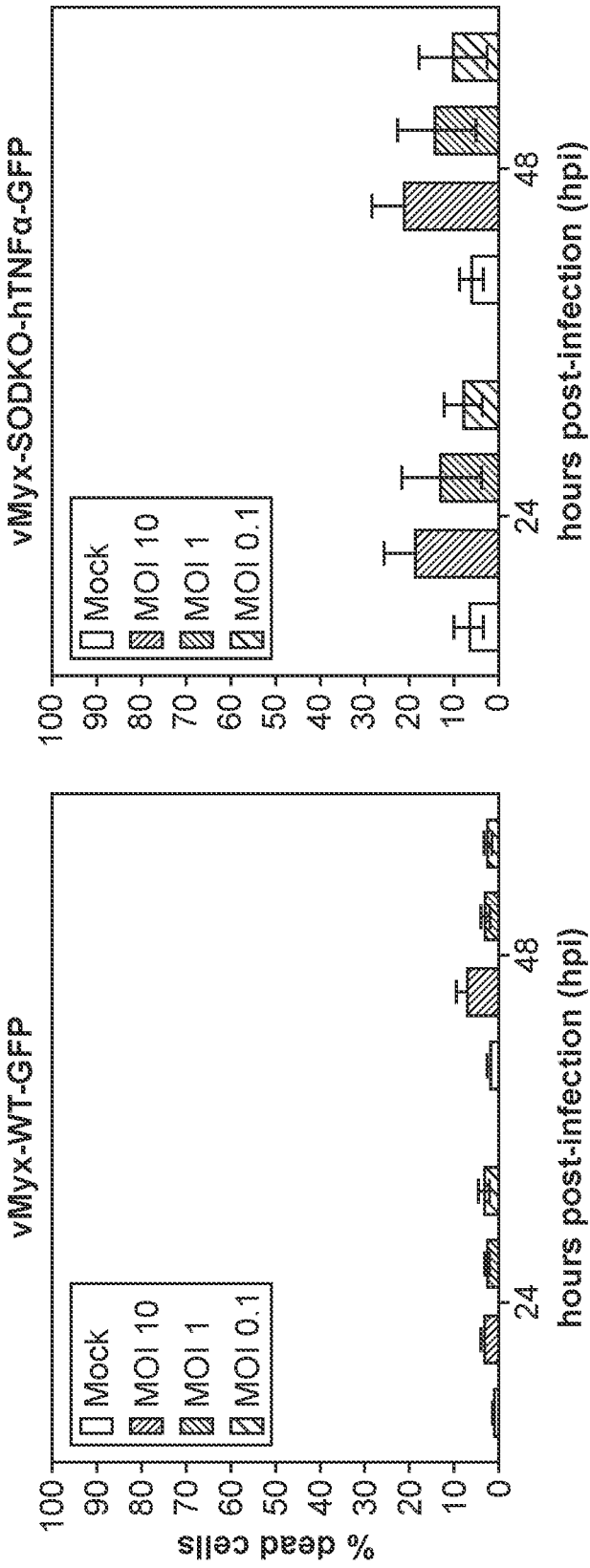
FIG. 12 illustrates quantification of cell death of infected human Multiple Myeloma (U266) cells using flow cytometry. MYXV-mediated total U266 killing was determined from the population of cells that were APC/Cy7+. Significance (*=p<0.05; =p<0.01; *=p<0.001) was determined using Holm-Sidak's t test for multiple comparisons.

FIG. 12 illustrates quantification of cell death of infected human Multiple Myeloma (U266) cells using flow cytometry. MYXV-mediated total U266 killing was determined from the population of cells that were APC/Cy7+. Significance (*=p<0.05; =p<0.01; *=p<0.001) was determined using Holm-Sidak's t test for multiple comparisons. The results show that infection of U266 cells with vMyx-SODKO-hTNF-GFP caused an overall increase in the number of gated dead cells at the 3 tested multiplicities of infection (MOI=10, 1 or 0.1) at both times post-infection (24 and 48 hrs).

FIG. 13 shows testing of vMyx-SODKO-hTNF delivered via ex vivo-loaded syngeneic murine bone marrow leukocytes to eliminate pre-seeded murine multiple myeloma in immunocompetent mice. Because the transgenic murine VK*MYC model of multiple myeloma is a very aggressive and drug resistant model, virotherapy with MYXV virus was used in conjunction with autologous stem cell transplantation (ASCT) with bone marrow leukocytes to improve cancer free survival rates. FIG. 13A shows in vivo data using bortezomib-resistant VK*12598 myeloma cells transplanted into C57/Bl mice, where they migrate mostly to the bone marrow and spleen. Briefly, $1 \times 10^6$ of VK*12598 myeloma cells were delivered into immunocompetent C57BL/6 mice intravenously via tail vain (i.v.). Four days post cancer delivery, mice were treated as follows: controls receiving no bone marrow (BM) transplant; $2 \times 10^6$ BM cells alone; $2 \times 10^6$ BM cells ex vivo pre-treated with vMyx-M135KO unarmed myxoma virus (MOI=10); $2 \times 10^6$ BM ex vivo treated with vMyx-SODKO-hTNF (M0I=10) via retro orbital (RO) injection. Survival curves were generated 100 days post cancer implantation (FIG. 13B). FIG. 13C corresponds to the percentages of survival.

FIG. 14 shows combination therapy with vMyx-hTNF-(M135-M136) pre-loaded ex vivo on BM leukocytes with either SMAC Mimetic or Immune Checkpoint Inhibitor. Combination therapy was tested with the SMAC mimetic compound LCL161 (50 mg/Kg), or the checkpoint inhibitor monoclonal antibody (mAb) α-muPD-1, combined with vMyx-hTNF-(M135-M136) delivered via ex vivo-preloaded autologous murine bone marrow leukocytes. Briefly, $1 \times 10^6$ of VK*12598 murine myeloma cells were delivered into immunocompetent C57BL/6 mice intravenously via tail vain (i.v.). After four weeks, we quantified the levels of myeloma protein marker in sera, (e.g., M-spike) using serum protein electrophoresis (SPEP). Mice were then treated with $2 \times 10^6$ BM cells that had been ex vivo pre-treated with vMyx-hTNF-(M135-M136) at MOI=10 at days 1, 4, 8 and 11. Each autologous transplant was followed by either chemotherapy with 50 mg/Kg of LCL161 delivered via oral gavage, or immunotherapy with 10 mg/Kg of the mAb α-muPD-1 at day 2, 5, 9, 12 via intraperitoneal (I.p.) injection. FIG. 14B shows in vivo data including the survival curves. FIG. 14C describes the percentages of survival.

Figure 15:
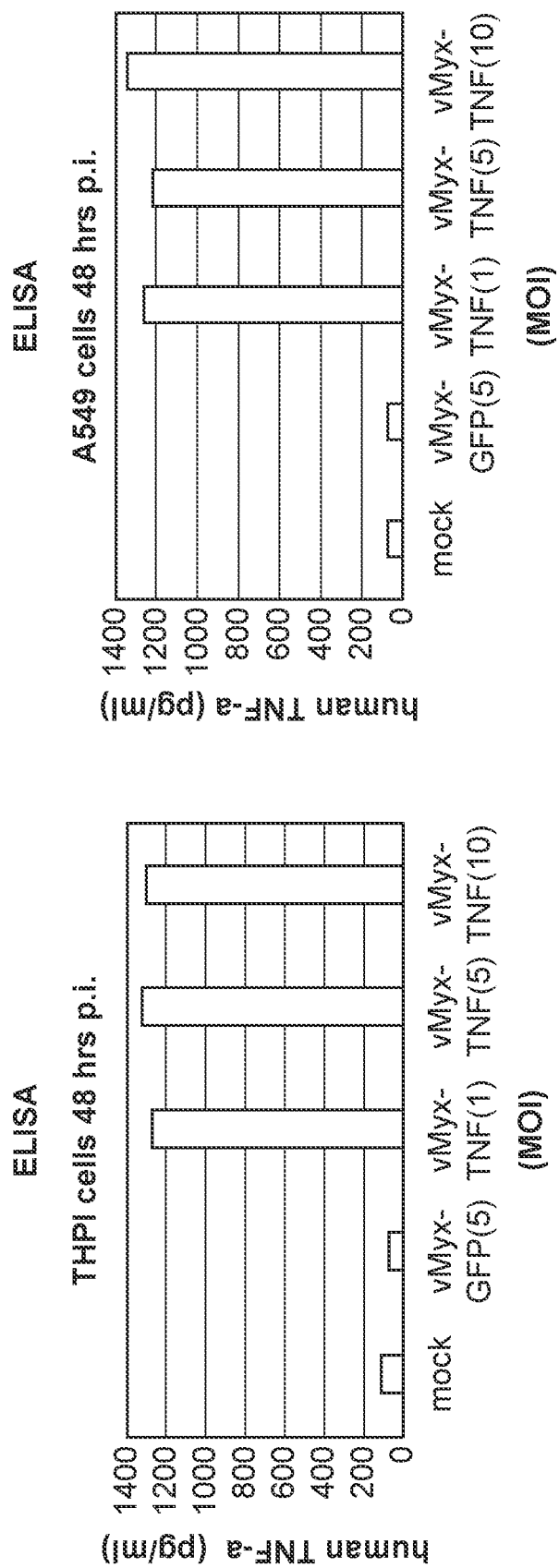
FIG. 15 shows human TNF protein expression and partial secretion from human cells infected with vMyx-hTNF-(M135-136).

FIG. 15 shows human TNF protein expression and partial secretion from human cells infected with vMyx-hTNF-(M135-136). Two human cell lines: THP1 (human monocytic) and A549 (human lung cancer) were infected with vMYX-hTNF-(M135-136) and control vMyx-GFP at three different multiplicities of infection (MOIs). After 48 hr post-infection, the supernatants were collected and the level of soluble human TNF secreted from the virus-infected cells was assayed by ELISA (Biolegend).

Example 5

The vMyx-hTNF-M135-M136 virus was created using the MYXV Lausanne parental strain. In brief, the vMyx-hTNF-M135-M136 virus was generated using the Multisite gateway three fragment cloning procedure. Element 1 contained 3' fragment of the M134R-partial and M135R ORF along with eGFP controlled by the synthetic early/late promoter. Element 2 contained the full hTNF coding sequence also under the control of the synthetic early/late promoter. Element 3 contained a fragment of the 5' M136R gene. These three fragments were combined into a single-entry vehicle plasmid that were used to insert the eGFP-hTNF tandem cassette at an intergenic location between the M135R and M136R gene in the MYXV genome backbone. This was then used for transfection/infection and recombinant virus was purified using at least 3 rounds of plaque purification (final plasmid used for transfection shown in FIG. 2B).

Exemplary sequences corresponding to the compositions and methods described herein are shown in Table 1.

TABLE 1

| SEQ ID NO | Name | Sequence |
|---|---|---|
| 1 | M134R-partial and M135R (utilized in vMyx-hTNF-M135-136) | ATGCTTTTTTATAATGCCAACTTTGTACAAAAAAGCAGGCT CCAGGATTACCTGGTCTATATAGATAACAAAACCTACGTAC GTATAAACGAGACCGTTGTACCGGAGAACGAGTATCTGGC AGCGAAGGCCCCGCGAGTGACCTGTTTCCACACGGACTTGA TCCCCATTACGGACGAAGAGACACAACGACGTTTTGAGAA AATGATTGTACAGGCGGCGTTAGAGGACGCCCTAACGAGC ATCTTTGAGGAGCACGACAATAACGTAACCGATTACTTCGC GGAATACATGCGATCCCTCCAAATGGCGAATAAAAGTCAT ACGAATAATATTATCGCGGTCGCTTTAGCGGGGATAATCGT CATTGTAACGACCTACGTGTTTACTAGATTACGCACTAAGC AAAAAAAAGGAAATTATAACGTACGTAATAAGATAGATAA TTCCATACAGAAAGAGATTCAGTTGGACGGTGTATATACTA CTGACAACGTTTTTATATAAACATGGTGTTTATATTTATTAT CACCTGNGTATGTTTGGTGACGAGATCCTGTGGGGGTGGGT TAGAAGACGATATAGATCGCATATTTCAAAAACGATACAA CGAACTGAGCCAGCCGATTAAGCGCAATATGCGTACACTGT GCAAGTTTAGAGGAATTACCGCGACTATGTTTACGGAAGG AGAATCTTACCTTATTCAATGTCCCATAATTCACGATTACGT GCTACGGGCGCTGTATGACTTAGTGGAAGGAAGTTACACG GTACGCTGGGAACGCGAAACGGAAGACGATGTTGAGTCGG TAGATCCGAAGTTAGTCAAAGGGACGCTATTATACCTCCAA CCTAACGCGTCCAGTATAGGAACGTATCTATGTACCTTACA CGATAACCGAGGTATGTGTTATCAATCTGTCGCGCACGTCA TCCGACGTCCGAAGATGCAATGCGTGAAACATGCACATAC |

TABLE 1-continued

| SEQ ID NO | Name | Sequence |
|---|---|---|
| | | GACATCGGACAGCAACCTGTGGATATACCTCGCCATTTTAG<br>CAGTTTTGATATCcttaggcgtcctgtaa |
| 2 | M136R | acgacgtaactccgaacTatgaagtaacattttttaaaacaa<br>tttcgttatgttaaattATGGAACGGTCGCCCACTTACACGG<br>TACACGATAAACGCTTTTCTATCGTCGCACTAAACGGACAAT<br>ACGACATGGTGGACGATTTTGGTCTTAGTTTTTCTTACACAG<br>CGATCGACGATATTTCTAAAAATCATTCCATCAAACACGTTT<br>TAGAAGAATACTTTTCATGGCGCGCGTATATAGGCCGGGTAT<br>GTATCATACCGAATCACGTGGGAAAGCTCTACATCAAACTTA<br>CAAAGTTGGACACCACGGCGAAGAACAAACTAGGCAATCTAG<br>ATATATTGTTATGCGACGTGTTAAAAATAGACGAGGACGGAG<br>GCAACGAGAAACTGTTTCAATTCATACGGTCGCTGAACCTAC<br>ACAAGAATAAAGAGAACACGTTGACGTTGATAGGATTACTAG<br>CCTACGCGTGCAACTTCTGGGGCAGTCAAAAAATAAATAAAT<br>ACATTCCTTCCATCATGCCGTTTTTCTTAAAACAAACGACCG<br>AGTCTATACTTTCCGAACTGTGTGTTATTTTGAACTATAACA<br>AATTGTATTAA |
| 3 | Synthetic early/<br>late promoter | TTAAAAATTGAAATTTTATTTTTTTTTTTGGAATATAAATA |
| 4 | hTNF | ATGAGCACTGAAAGCATGATCCGGGACGTGGAGCTGGCCG<br>AGGAGGCGCTCCCCAAGAAGACAGGGGGGCCCCAGGGCTC<br>CAGGCGGTGCTTGTTCCTCAGCCTCTTCTCCTTCCTGATCGT<br>GGCAGGCGCCACCACGCTCTTCTGCCTGCTGCACTTTGGAG<br>TGATCGGCCCCAGAGGGAAGAGTTCCCCAGGGACCTCTCT<br>CTAATCAGCCCTCTGGCCCAGGCAGTCAGATCATCTTCTCG<br>AACCCCGAGTGACAAGCCTGTAGCCCATGTTGTAGCAAACC<br>CTCAAGCTGAGGGGCAGCTCCAGTGGCTGAACCGCCGGGC<br>CAATGCCCTCCTGGCCAATGGCGTGGAGCTGAGAGATAAC<br>CAGCTGGTGGTGCCATCAGAGGGCCTGTACCTCATCTACTC<br>CCAGGTCCTCTTCAAGGGCCAAGGCTGCCCCTCCACCCATG<br>TGCTCCTCACCCACACCATCAGCCGCATCGCCGTCTCCTAC<br>CAGACCAAGGTCAACCTCCTCTCTGCCATCAAGAGCCCCTG<br>CCAGAGGGAGACCCCAGAGGGGGCTGAGGCCAAGCCCTGG<br>TATGAGCCCATCTATCTGGGAGGGGTCTTCCAGCTGGAGAA<br>GGGTGACCGACTCAGCGCTGAGATCAATCGGCCCGACTATC<br>TCGACTTTGCCGAGTCTGGGCAGGTCTACTTTGGGATCATT<br>GCCCTGTGA |
| 5 | eGFP | ATGGTGAGCAAGGGCGAGGAGCTGTTCACCGGGGTGGTGC<br>CCATCCTGGTCGAGCTGGACGGCGACGTAAACGGCCACAA<br>GTTCAGCGTGTCCGGCGAGGGCGAGGGCGATGCCACCTAC<br>GGCAAGCTGACCCTGAAGTTCATCTGCACCACCGGCAAGCT<br>GCCCGTGCCCTGGCCCACCCTCGTGACCACCCTGACCTACG<br>GCGTGCAGTGCTTCAGCCGCTACCCCGACCACATGAAGCAG<br>CACGACTTCTTCAAGTCCGCCATGCCCGAAGGCTACGTCCA<br>GGAGCGCACCATCTTCTTCAAGGACGACGGCAACTACAAG<br>ACCCGCGCCGAGGTGAAGTTCGAGGGCGACACCCTGGTGA<br>ACCGCATCGAGCTGAAGGGCATCGACTTCAAGGAGGACGG<br>CAACATCCTGGGGCACAAGCTGGAGTACAACTACAACAGC<br>CACAACGTCTATATCATGGCCGACAAGCAGAAGAACGGCA<br>TCAAGGTGAACTTCAAGATCCGCCACAACATCGAGGACGG<br>CAGCGTGCAGCTCGCCGACCACTACCAGCAGAACACCCCC<br>ATCGGCGACGGCCCCGTGCTGCTGCCCGACAACCACTACCT<br>GAGCACCCAGTCCGCCCTGAGCAAAGACCCCAACGAGAAG<br>CGCGATCACATGGTCCTGCTGGAGTTCGTGACCGCCGCCGG<br>GATCACTCTCGGCATGGACGAGCTGTACAAGTAA |
| 6 | M134-partial and<br>M135R partial<br>(utilized in vMyx-<br>M135KO-hTNF) | CGAGGATTACCTGGTCTATATAGATAACAAAACCTACGTAC<br>GTATAAACGAGACCGTTGTACCGGAGAACGAGTATCTGGC<br>AGCGAAGGCCCCGCGAGTGACCTGTTTCCACACGGACTTGA<br>TCCCCATTACGGACGAAGAGACACAACGACGTTTTGAGAA<br>AATGATTGTACAGGCGGCGTTAGAGGACGCCCTAACGAGC<br>ATCTTTGAGGAGCACGACAATAACGTAACCGATTACTTCGC<br>GGAATACATGCGATCCCTCCAAATGGCGAATAAAAGTCAT<br>ACGAATAATATTATCGCGGTCGCTTTAGCGGGGATAATCGT<br>CATTGTAACGACCTACGTGTTTACTAGATTACGCACTAAGC<br>AAAAAAAAGGAAATTATAACGTACGTAATAAGATAGATAA<br>TTCCATACAGAAAGAGATTCAGTTGGACGGTGTATATACTA<br>CTGACAACGTTTTTATATAAACATGGTGTTTATATTTATTAT<br>CACCTGTGTATGTTTGGTGACGAGATCCTGTGGGGGTGGGT<br>TAGAAGACGATATAGATCGC |

In some instances, the MYXV (Lausanne strain) comprises a sequence as illustrated by GenBank: AF170726.2 (which is hereby incorporated by reference as provided by GenBank on Jul. 11, 2019).

In some instances, vMyx-hTNF-M135-136 comprises SEQ ID NOs: 1-5, arranged as shown in FIG. 2B. In some cases, vMyx-hTNF-M135-136 comprises a Lausanne strain backbone, optionally comprising the sequence as illustrated by GenBank: AF170726.2.

In some instances, vMyx-M135KO-hTNF comprises SEQ ID NOs: 6, 2, 4, and 5, arranged as shown in FIG. 2A. In some cases, vMyx-M135KO-hTNF comprises a Lausanne strain backbone, optionally comprising the sequence as illustrated by GenBank: AF170726.2.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A pharmaceutical composition comprising a myxoma virus (MYXV) and a pharmaceutically-acceptable excipient, wherein the MYXV is engineered to express a tumor necrosis factor (TNF) protein, wherein a gene encoding the TNF protein is inserted between M134 gene and M136 gene within the MYXV genome.

2. The pharmaceutical composition of claim 1, wherein the TNF protein is a TNF alpha protein.

3. The pharmaceutical composition of claim 1, wherein the TNF protein is a cell surface expressed TNF protein.

4. The pharmaceutical composition of claim 1, wherein the TNF protein is secreted by cells infected by the MYXV.

5. The pharmaceutical composition of claim 1, wherein the TNF protein is a human TNF protein.

6. The pharmaceutical composition of claim 1, wherein the MYXV is a genetically modified Laussane strain MYXV.

7. The pharmaceutical composition of claim 1, wherein the pharmaceutical composition is formulated for systemic administration.

8. The pharmaceutical composition of claim 1, wherein the pharmaceutical composition is formulated for local administration.

9. The pharmaceutical composition of claim 1, wherein the pharmaceutical composition is formulated for parenteral administration.

10. The pharmaceutical composition of claim 1, wherein the MYXV is capable of directly killing cancer cells infected by the MYXV and eliciting off-target killing of uninfected cancer cells.

11. The pharmaceutical composition of claim 10, wherein the MYXV exhibits enhanced off-target killing of uninfected cancer cells as compared to a MYXV that is not engineered to express the TNF protein.

12. A composition comprising peripheral blood mononuclear cells (PBMCs), bone marrow (BM) cells, or a combination thereof treated ex vivo by a myxoma virus (MYXV) engineered to express a tumor necrosis factor (TNF) protein, wherein a gene encoding the TNF protein is inserted between M134 gene and M136 gene within the MYXV genome.

13. The composition of claim 12, wherein the MYXV comprises a modification within or adjacent to one or more genes associated with rabbit cell tropism.

14. The composition of claim 12, wherein the MYXV comprises a modification of M135R that impairs function of the M135R.

15. A method of inhibiting or treating a cancer in a subject in need thereof, comprising administering to the subject a pharmaceutical composition comprising a myxoma virus (MYXV) and a pharmaceutically-acceptable excipient, wherein the MYXV is engineered to express a tumor necrosis factor (TNF) protein, wherein a gene encoding the TNF protein is inserted between M134 gene and M136 gene within the MYXV genome.

* * * * *

SEQUENCE LISTING

```
<160> NUMBER OF SEQ ID NOS: 6

<210> SEQ ID NO 1
<211> LENGTH: 1046
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (536)..(536)
<223> OTHER INFORMATION: a, c, t, g, unknown or other

<400> SEQUENCE: 1
atgctttttt ataatgccaa ctttgtacaa aaaagcaggc tccaggatta cctggtctat     60
atagataaca aaacctacgt acgtataaac gagaccgttg taccggagaa cgagtatctg    120
gcagcgaagg ccccgcgagt gacctgtttc cacacggact tgatccccat tacggacgaa    180
gagacacaac gacgttttga gaaaatgatt gtacaggcgg cgttagagga cgccctaacg    240
agcatctttg aggagcacga caataacgta accgattact tcgcggaata catgcgatcc    300
ctccaaatgg cgaataaaag tcatacgaat aatattatcg cggtcgcttt agcggggata    360
atcgtcattg taacgaccta cgtgtttact agattacgca ctaagcaaaa aaaaggaaat    420
tataacgtac gtaataagat agataattcc atacagaaag agattcagtt ggacggtgta    480
tatactactg acaacgtttt tatataaaca tggtgtttat atttattatc acctgngtat    540
gtttggtgac gagatcctgt gggggtgggt tagaagacga tatagatcgc atatttcaaa    600
aacgatacaa cgaactgagc cagccgatta agcgcaatat gcgtacactg tgcaagttta    660
gaggaattac cgcgactatg tttacggaag gagaatctta ccttattcaa tgtcccataa    720
ttcacgatta cgtgctacgg gcgctgtatg acttagtgga aggaagttac acggtacgct    780
gggaacgcga aacggaagac gatgttgagt cggtagatcc gaagttagtc aaagggacgc    840
tattatacct ccaacctaac gcgtccagta taggaacgta tctatgtacc ttacacgata    900
accgaggtat gtgttatcaa tctgtcgcgc acgtcatccg acgtccgaag atgcaatgcg    960
tgaaacatgc acatacgaca tcggacagca acctgtggat atacctcgcc attttagcag   1020
ttttgatatc cttaggcgtc ctgtaa                                         1046

<210> SEQ ID NO 2
<211> LENGTH: 599
<212> TYPE: DNA
<213> ORGANISM: Myxoma virus

<400> SEQUENCE: 2
```

```
acgacgtaac tccgaactat gaagtaacat tttttaaaac aatttcgtta tgttaaatta      60
tggaacggtc gcccacttac acggtacacg ataaacgctt ttctatcgtc gcactaaacg     120
gacaatacga catggtggac gattttggtc ttagttttc ttacacagcg atcgacgata     180
tttctaaaaa tcattccatc aaacacgttt tagaagaata cttttcatgg cgcgcgtata     240
taggccgggt atgtatcata ccgaatcacg tgggaaagct ctacatcaaa cttacaaagt     300
tggacaccac ggcgaagaac aaactaggca atctagatat attgttatgc gacgtgttaa     360
aaatagacga ggacggaggc aacgagaaac tgtttcaatt catacggtcg ctgaacctac     420
acaagaataa agaaacacg ttgacgttga taggattact agcctacgcg tgcaacttct     480
ggggcagtca aaaataaat aaatacattc cttccatcat gccgttttc ttaaaacaaa     540 cgaccgagtc tatactttcc gaactgtgtg ttattttgaa ctataacaaa ttgtattaa     599
```

<210> SEQ ID NO 3
<211> LENGTH: 42
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 3

```
ttaaaaattg aaattttatt ttttttttt ggaatataaa ta                         42
```

<210> SEQ ID NO 4
<211> LENGTH: 702
<212> TYPE: DNA
<213> ORGANISM: Homo sapiens

<400> SEQUENCE: 4

```
atgagcactg aaagcatgat ccgggacgtg gagctggccg aggaggcgct ccccaagaag      60 acagggggc cccagggctc caggcggtgc ttgttcctca gcctcttctc cttcctgatc     120
gtggcaggcg ccaccacgct cttctgcctg ctgcactttg gagtgatcgg ccccccagagg     180 gaagagttcc ccaggaccct ctctctaatc agccctctgg cccaggcagt cagatcatct     240
tctcgaaccc cgagtgacaa gcctgtagcc catgttgtag caaaccctca agctgagggg     300
cagctccagt ggctgaaccg ccgggccaat gccctcctgg ccaatggcgt ggagctgaga     360
gataaccagc tggtggtgcc atcagagggc ctgtacctca tctactccca ggtcctcttc     420
aagggccaag gctgccctc cacccatgtg ctcctcaccc acaccatcag ccgcatcgcc     480
gtctcctacc agaccaaggt caacctcctc tctgccatca gagcccctg ccagagggag     540 accccagagg gggctgaggc caagccctgg tatgagccca tctatctggg aggggtcttc     600
cagctggaga agggtgaccg actcagcgct gagatcaatc ggcccgacta tctcgacttt     660
gccgagtctg gcaggtcta ctttgggatc attgccctgt ga                         702
```

<210> SEQ ID NO 5
<211> LENGTH: 720
<212> TYPE: DNA
<213> ORGANISM: Artificial Sequence
<220> FEATURE:
<223> OTHER INFORMATION: Description of Artificial Sequence: Synthetic
     polynucleotide

<400> SEQUENCE: 5

```
atggtgagca aggcgagga gctgttcacc ggggtggtgc ccatcctggt cgagctggac      60
ggcgacgtaa acggccacaa gttcagcgtg tccggcgagg gcgagggcga tgccacctac     120
```

```
ggcaagctga ccctgaagtt catctgcacc accggcaagc tgcccgtgcc ctggcccacc      180
ctcgtgacca ccctgaccta cggcgtgcag tgcttcagcc gctacccccga ccacatgaag      240 cagcacgact tcttcaagtc cgccatgccc gaaggctacg tccaggagcg caccatcttc      300
ttcaaggacg acggcaacta caagacccgc gccgaggtga agttcgaggg cgacaccctg      360
gtgaaccgca tcgagctgaa gggcatcgac ttcaaggagg acggcaacat cctggggcac      420
aagctggagt acaactacaa cagccacaac gtctatatca tggccgacaa gcagaagaac      480
ggcatcaagg tgaacttcaa gatccgccac aacatcgagg acggcagcgt gcagctcgcc      540
gaccactacc agcagaacac ccccatcggc gacggccccg tgctgctgcc cgacaaccac      600
tacctgagca cccagtccgc cctgagcaaa gaccccaacg agaagcgcga tcacatggtc      660
ctgctggagt tcgtgaccgc cgccgggatc actctcggca tggacgagct gtacaagtaa      720

<210> SEQ ID NO 6
<211> LENGTH: 549
<212> TYPE: DNA
<213> ORGANISM: Myxoma virus

<400> SEQUENCE: 6
cgaggattac ctggtctata tagataacaa aacctacgta cgtataaacg agaccgttgt       60
accggagaac gagtatctgg cagcgaaggc cccgcgagtg acctgtttcc acacggactt      120
gatccccatt acgacgaag agacacaacg acgtttttgag aaaatgattg tacaggcggc      180
gttagaggac gccctaacga gcatctttga ggagcacgac aataacgtaa ccgattactt      240
cgcggaatac atgcgatccc tccaaatggc gaataaaagt catacgaata atattatcgc      300
ggtcgcttta gcggggataa tcgtcattgt aacgacctac gtgtttacta gattacgcac      360
taagcaaaaa aaaggaaatt ataacgtacg taataagata gataattcca tacagaaaga      420
gattcagttg gacggtgtat atactactga caacgttttt atataaacat ggtgtttata      480
tttattatca cctgtgtatg tttggtgacg agatcctgtg ggggtgggtt agaagacgat      540
atagatcgc                                                              549
```